(12) United States Patent
Nielsen et al.

(10) Patent No.: US 6,350,853 B1
(45) Date of Patent: Feb. 26, 2002

(54) CONJUGATED PEPTIDE NUCLEIC ACIDS HAVING ENHANCED CELLULAR UPTAKE

(75) Inventors: Peter E. Nielsen, Hjortevanget 509, Kokkedal; Helle Knudsen, Copenhagen, both of (DK)

(73) Assignee: Peter E. Nielsen (DK)

( * ) Notice: Subject to any disclaimer, the term of this patent is extended or adjusted under 35 U.S.C. 154(b) by 0 days.

(21) Appl. No.: 09/404,430

(22) Filed: Sep. 23, 1999

Related U.S. Application Data

(63) Continuation of application No. PCT/US98/10804, filed on May 28, 1998, which is a continuation-in-part of application No. 08/864,765, filed on May 28, 1997, now abandoned, which is a continuation-in-part of application No. 08/595,387, filed on Feb. 1, 1996, now Pat. No. 5,773,571, which is a continuation-in-part of application No. 08/054,363, filed on Apr. 26, 1993, now Pat. No. 5,539,082.

(51) Int. Cl.$^7$ ...................... A61K 9/127; A61K 31/712; A61K 38/02; C07H 21/00; C07K 2/00

(52) U.S. Cl. .................. 530/300; 536/23.1; 536/24.3; 536/24.5; 424/450

(58) Field of Search ...................... 435/6, 375; 514/44; 530/300, 333, 335, 337, 345; 536/22.1, 23.1, 24.3, 24.5; 532/818; 549/223; 585/352; 424/450

(56) References Cited

U.S. PATENT DOCUMENTS

| | | | |
|---|---|---|---|
| 5,539,082 A | 7/1996 | Nielsen et al. | 530/300 |
| 5,578,718 A | 11/1996 | Cook et al. | 536/27.21 |
| 5,595,978 A | 1/1997 | Draper et al. | 514/44 |
| 5,773,571 A | 6/1998 | Nielsen et al. | 530/300 |

FOREIGN PATENT DOCUMENTS

| | | |
|---|---|---|
| WO | WO 92/20702 | 11/1992 |
| WO | WO 92/20703 | 11/1992 |
| WO | WO 93/12129 | 6/1993 |
| WO | WO 94/06815 | 3/1994 |
| WO | WO 96/02558 | 2/1996 |
| WO | WO 96/10391 | 4/1996 |
| WO | WO 96/24334 | 8/1996 |
| WO | WO 96/39531 | 12/1996 |
| WO | WO 96/40627 | 12/1996 |
| WO | WO 97/14026 | 4/1997 |

OTHER PUBLICATIONS

Anderson et al., "t–Butyloxycarbonylamino Acids and Their Use in Peptide Synthesis" *J. Am. Chem. Soc.*, 1957, 79, 6180–6183.

Barany et al. in "The Peptides", Academic Press, New York, vol. 2, 1979, p. 1–284.

Barany et al., "Solid–phase peptide synthesis: a silver anniversary report", *Int. J. Peptide Protein Res.*, 1987, 30, 705–739.

Barany et al.,"A New Amino Protecting Group Removable by Reduction. Chemistry of the Dithiasuccinoyl (Dts) Function", *J. Am. Chem. Soc.*, 1977, 99, 7363–7365.

Barton et al., "Solid–phase synthesis of selectively protected peptides for use as building units in the solid–phase synthesis of large molecules", *J. Am. Chem. Soc.*, 1973, 95, 4501–4506.

Best et al., "Energetics of Formation of Sixteen Triple Helical Complexes Which Vary at a Single Position within a Pyrimidine Motif", *J. Am. Chem. Soc.*, 1995, 117, 1187–1193.

Blume et al., "Liposomes for the sustained drug release in vivo", *Biochem. et Biophys. Acta*, 1990, 1029, 91–97.

Bodanszky et al., "Active esters and resins in peptide synthesis", *Chem. Ind.*, 1964, 1423–1424.

Brady et al., "Some Novel, Acid–Labile Amine Protecting Groups", *J. Org. Chem.*, 1977, 42, 143–146.

Buchardt et al., "Peptide nucleic acids and their potential applications in biotechnology," *TIBTECH*, 1993, 11, 384–386.

Campbell, "Lipofection Reagents Prepared by a Simple Ethanol Injection Technique", *Biotechniques*, 1995, 18(6), 1027–1032.

Carpino et al., "The 9–Fluorenylmethoxycarbonyl Function, a New Base–Sensitive Amino–Protecting Group" *J. Am. Chem. Soc.*, 1970, 92, 5748–5749.

Carpino et al., "The 9–Fluorenylmethoxycarbonyl Amino–Protecting Group", *J. Org. Chem.*, 1972, 22, 3404–3409.

Carpino, "Oxidative Reactions of Hydrazines. IV. Elimination of Nitrogen from 1,1–Disubstituted–2–arenesulfonhydrazides", *J. Am. Chem. Soc.*, 1957, 79, 4427–4431.

Chonn et al., "Recent advances in liposomal drug–delivery systems", *Curr. Opin. Biotech.*, 1995, 6, 698–708.

Dueholm, "Synthesis of Peptide Nucleic Acid Monomers Containing the Four Natural Nucleobases: Thymine, Cytosine, Adenine, and Guanine and Their Oligomerization", *J. Org. Chem.*, 1994, 59, 5767–5773.

Dueholm et al., "An Efficient Synthesis of BOC–Aminoacetaldehyde and its Application to the Synthesis of N–(2–BOC–Aminoethyl)Glycine Esters", *Organic Prep. & Proc.*, 1993, 25, 457–461.

Egholm et al., "PNA hybridizes to complementary oligonucleotides obeying the Watson–Crick hydrogen bonding rules", *Nature*, 1993, 365, 566–568.

(List continued on next page.)

*Primary Examiner*—John L. LeGuyader
*Assistant Examiner*—Thomas G Larson
(74) *Attorney, Agent, or Firm*—Woodcock Washburn LLP

(57) ABSTRACT

Peptide nucleic acids conjugated to lipophilic groups and incorporated into liposomes exhibit enhanced cellular uptake and distribution. Cellular uptake and distribution of peptide nucleic acids also increases with the introduction of an amino acid side chain into the backbone of peptide nucleic acids. Methods of modulating cellular uptake and methods for treating animals are provided. The peptide nucleic acids of the invention comprise naturally-occurring nucleobases and non-naturally-occurring nucleobases attached to a polyamide backbone.

8 Claims, 1 Drawing Sheet

OTHER PUBLICATIONS

Egholm, "Peptide Nucleic Acids (PNA). Oligonucleotide Analogues with an Achiral Peptide Backbone", *J. Am. Chem. Soc.*, 1992, 114, 1895–1897.

Egholm et al., "Recognition of Guanine and Adenine inDNA by Cytosine and Thymine Containing Peptide Nucleic Acids (PNA)", *J. Am. Chem. Soc.*, 1992, 114, 9677–9678.

Ettinger et al., "Intrathecal Methotrexate Overdose Without Neurotoxicity", *Cancer*, 1978, 41, 1270–1273.

Ewel et al., "Polyinosinic–Polycytidylic Acid Complexed with Poly–L–lysine and Corboxymethylcellulose in Combination with Interleukin 2 in Patients with Cancer: Clinical and Immunological Effects", *Cancer Res.*, 1992, 52, 3005–3010.

Fraley et al., "New generation liposomes: the engineering of an efficient vehicle for intracellular delivery of nucleic acids", *Trends Biohcem. Sci.*, 1981, 6, 77–80.

Goodman et al., "Peptide Synthesis via Active Esters. IV. Racemization and Ring–Opening Reactions of Optically Active Oxazolones", *J. Am. Chem. Soc.*, 1964, 86, 2918–2922.

Greenberg et al., "Energetics of Formation of Sixteen Triple Helical Compleses Which Cary at a Single Position within a Purine Motif", *J. Am. Chem. Soc.*, 1995, 117, 5016–5022.

Gregoridadis, G. (Eds.) in "Liposome Technology", CRC Press, vol. 2, 1993.

Haas et al., "Adamantyloxycarbonyl, a New Blocking Group. Preparation of 1–Adamantyl Chloroformate", *J. Am. Chem. Soc.*, 1966, 88, 1988–1992.

Hyrup et al., "Peptide Nucleic Acids (PNA): Synthesis, Properties, and Potential Applications", *Biorg. & Med. Chem.*, 1996, 4, 5–23.

Jones, "Hydrogenation of Protected Leucine Enkephalin from a Resin During Solid Phase Synthesis", *Tetrahedron Letts.*, 1977, 33, 2853–2856.

Kemeny et al., "A Pilot Study of Hepatic Artery Floxuridine Combined with Systemic 5–Fluorouricil and Leucovorin", *Cancer*, 1993, 71, 1964–1971.

Kemp et al., "New Protective Groups for Peptide Synthesis—I. The BIC Group Base and Solvent Lability", *Tetrahedron Letts.*, 1975, 52, 4625–4628.

Knudson et al., "Antisense Properties of duplex–and triple–forming PNA", *Nucl. Acids Res.*, 1996, 24, 494–500.

Konig et al., "Racemisierung bei Peptidsynthesen" *Chem. Ber.*, 1970, 103, 2024–2033.

Konig et al., "Eine neue Methode zur Synthesis von Peptiden: Aktivierung der Carboxylgruppe mit Dicyclohexylcarbodiimide und 3–Hydroxy–4–oxo–3, 4–dihydro–1.2.3–benzotriazin", *Chem. Ber.*, 1970, 103, 2034–2040.

Kovacs et al., "Glutamic and Aspartic Anhydrides. Rearrangement of N–Carboxyglutamic 1,5–Anhydride to the Leuchs' Anhydride and Conversion of the Latter to Pyroglutamic Acid", *J. Am. Chem. Soc.*, 1963, 85, 1839–1844.

Lappalainen et al., "Cationic liposomes mediated delivery of antisense oligonucleotides targeted to HPV 16 E7 mRNA in CaSki cells", *Antiviral Res.*, 1994, 23, 119–130.

Li et al., "The Synthesis of a Protein Possessing Growth–Promoting and Lactogenic Activities", *J. Am. Chem. Soc.*, 1970, 92, 7608–7609.

Luer et al., "Vancomycin Administration into the Cerebrospinal Fluid: A Review", *Annals Pharmacother.*, 1993, 27, 912–921.

McKay et al., "New Amine–Masking Groups for Peptide Synthesis", *J. Am. Chem. Soc.*, 1957, 79, 4686–4690.

Mannino et al., "Liposome Mediated Gene Transfer", *Biotech.*, 1988, 6(7), 682–690.

Merrifield, "Solid Phase Peptide Synthesis. I. The Synthesis of a Tetrapeptide", *J. Am. Chem. Soc.*, 1963, 85, 2149–2154.

Merrifield, "Solid Phase Synthesis", *Science*, 1986, 232, 341–347.

Morishita et al., "Single intraluminal delivery of antisense cdc2 kinase and proliferating–cell nuclear antigen oligonucleotides results in chronic inhibition of neointimal hyperplasia", *Proc. Natl. Acad. Sci USA.*, 1993, 90, 8474–8478.

Moser et al., "Sequence–Specific Cleavage of Double Helical DNA by Triple Helix Formation", *Science*, 1987, 238, 645–650.

Nefkens et al., "A Novel Activated Ester in Peptide Synthesis", *J. Am. Chem. Soc.*, 1961, 83, 1263.

Nielsen et al., "Sequence–Selective Recognition of DNA by Strand Displacement with a Thymine–Substituted Polyamide", *Science*, 1991, 254, 1497–1500.

Nielsen et al., "Strand Displacement to Binding of a Duplex– Forming Homopurine PNA to a Homopyrimidine Duplex DNA Target", *J. Am. Chem. Soc.*, 1996, 118, 2287–2288.

Nielsen, "Peptide nucleic acid (PNA): A lead for gene therapeutic drugs", *Perspectives Drug Disc. Des.*, 1996, 4, 76–84.

Patel, "Marriage of Convenience", *Nature*, 1993, 365, 490–492.

PCT International Search Report dated Sep. 16, 1998, 4 pages.

Pless et al., "Uber die Geschwindigkeit der Aminolyse von verschiedenen neuen, aktievierten, N–geschuzten α–Aminosaure–phenylestern insbesondere 2,4,5–Trichlorphenylestern", *Helv. Chim. Acta*, 1963, 46, 1609–1625 (English summary included).

Rich et al., "Preparation of a New o–Nitrobenzyl Resin for Solid Phase Synthesis of tert–Butyloxycarbonyl–Protected Peptide Acids", *J. Am. Chem. Soc.*, 1975, 97, 1575–1579.

Rivaille et al., "Synthesis of LH–RH Using a New Phenolic Polymer as Solid Support and 'BOP' Reagent for Fragment Coupling", *Tetrahedron*, 1980, 36, 3413–3419.

Rubenstein et al., "Antisense Oligonucleotide Intralesional Therapy for Human PC–3 Prostate Tumors Carried in Athymic Nude Mice", *J. Surg. Oncol.*, 1996, 62, 194–200.

Sakakibara et al., "A New Method for Releasing Oxytocin from Fully–protected Nona–peptides Using Anhydrous Hydrogen Fluoride", *Bull. Chem. Soc. Jpn.*, 1965, 38, 1412–1413.

Schlatter et al., "Hydrogenation in Solid Phase Peptide Synthesis. I. Removal of Product from the Resin", *Tetrahedron Letts.*, 1977, 33, 2851–2852.

Shaw, "Treatment of Intractable Cancer Pain by Electronically Controlled Parenteral Infusion of Analgesic Drugs", *Cancer*, 1993, 72(11 Suppl.), 3416–3425.

Sheehan et al., "A New Method of Forming Peptide Bonds", *J. Am. Chem. Soc.*, 1955, 77, 1067–1068.

Sieber, "Selektive acidolytische Spaltung von Aralkyloxcarbonyl–Aminoschutzgruppen", *Helv. Chim. Acta.*, 1968, 51, 614–622 (English summary included).

Stewart et al. in "Solid Phase Peptide Synthesis", 2nd ed., Pierce Chemical Company, Illinois, 1984.

Tam et al., "$S_{N^2}$ Deprotection of Synthetic Peptides with a Low Concentration of HF in Dimethyl Sulfide: Evidence and Application in Peptide Synthesis", *J. Am. Chem. Soc.*, 1983, 105, 6442–6455.

Tam et al., "Mechanisms for the Removal of Benzyl Protecting Groups in Synthetic Peptides by Trifluoromethansulfonic Acid–Trifluoroacetic Acid–Dimethyl Sulfide", *J. Am. Chem. Soc.*, 1986, 108, 5242–5251.

Uhlmann et al., "Antisense Oligonucleotides: A New Therapeutic Principle", *Chem. Reviews*, 1990, 90, 544–584.

Waldmann et al., "Allyester als selektiv abspaltbare carboxyschutzgruppen in der Peptid–und N–Glycopeptidsynthese", *Liebigs Ann. Chem.*, 1983, 1712–1715.

Watwe et al., "Manufacture of liposomes: A review", *Curr. Sci.*, 1995, 68(7), 715–724.

Wieland et al., "Symmetrical Boc–Amino Acid Anhydrides for Economical Peptide Synthesis on a Solid Phase", *Angew. Chem., Int. Ed. Engl.*, 1971, 10(5), 336.

Yaida et al., "Distribution of phosphodiester and phosphorothioate oligonucleotides in rat brain after intraventricular and intrahippocampal administration determined by in situ hybridization", *Regulatory Peptides*, 1995, 59, 193–199.

Yajima et al., "Trifluromethanesulphonic Acid as a Deprotecting Reagent in Peptide Chemistry", *J. Chem. Soc., Chem. Comm.*, 1974, 107–108.

Zervas et al., "New Methods in Peptide Synthesis. I. Tritylsulfenyl and o–Nitrophenylsulfenyl Groups as N–Protecting Groups", *J. Am. Chem. Soc.*, 1963, 85, 3660–3666.

Zimm et al., "Cerebrospinal Fluid Pharmacokinetics of Intravetricular and Intravenous Aziridinylbenzoquinone", *Cancer Res.*, 1984, 44, 1698–1701.

Examples of lipophilic groups

SEQUENCE LISTING

<160> NUMBER OF SEQ ID NOS: 5

<210> SEQ ID NO 1
<211> LENGTH: 14
<212> TYPE: DNA

```
-continued

<213> ORGANISM: Artificial Sequence
<220> FEATURE:
<223> OTHER INFORMATION: Description of Artificial Sequence: Novel
      Sequence

<400> SEQUENCE: 1
tagcagagga gctc                                                      14

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 2
ggtgctcact gcggc                                                     15

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 3
tttagcttca gc                                                        12

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4
tatttttttt                                                           10

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5
ggtgctcacg ctggc                                                     15
```

CONJUGATED PEPTIDE NUCLEIC ACIDS HAVING ENHANCED CELLULAR UPTAKE

This patent application is a continuation of Interational patent application PCT/US98/10804, filed on May 28, 1998, which is a continuation-in-part of application Ser. No. 08/864,765, filed on May 28, 1997 (now abandoned) which is a continuation-in-part of application Ser. No. 08/595,387, filed on Feb. 1, 1996 (now U.S. Pat. No. 5,773,571), which is a continuation-in-part of Ser. No. 08/054,363, filed on Apr. 26, 1993 (now U.S. Pat. No. 5,539,082).

FIELD OF THE INVENTION

The present invention is directed to compositions comprising a peptide nucleic acid (PNA) which is conjugated to a lipophilic group and incorporated into liposomes. The PNA is composed of naturally-occurring nucleobases or non-naturally-occurring nucleobases which are covalently bound to a polyamide backbone. The PNA compositions of the present invention may further comprise a PNA modified by an amino acid side chain. The PNA compositions of the present invention exhibit enhanced cellular uptake and distribution. PNA compositions which were incorporated into liposomes demonstrated increased cellular uptake and more diffuse distnbution than PNA compositions without liposomes.

BACKGROUND OF THE INVENTION

The function of a gene starts by transcription of its information to a messenger RNA (mRNA). By interacting with the ribosomal complex, mRNA directs synthesis of proteins. This protein synthesis process is known as translation. Translation requires the presence of various cofactors, building blocks, amino acids and transfer RNAs (tRNAs), all of which are present in normal cells.

Most conventional drugs exert their effect by interacting with and modulating one or more targeted endogenous proteins, e.g., enzymes. Typically, however, such drugs are not specific for targeted proteins but interact with other proteins as well. Thus, use of a relatively large dose of drug is necessary to effectively modulate the action of a particular protein. If the modulation of a protein activity could be achieved by interaction with or inactivation of mRNA, a dramatic reduction in the amount of drug necessary and in the side-effects of the drug could be achieved. Further reductions in the amount of drug necessary and the side-effects could be obtained if such interaction is site-specific. Since a functioning gene continually produces mRNA, it would be even more advantageous if gene transcription could be arrested in its entirety. Oligonucleotides and their analogs have been developed and used as diagnostics, therapeutics and research reagents. One example of a modification to oligonucleotides is labeling with non-isotopic labels, e.g., fluorescein, biotin, digoxigenin, alkaline phosphatase, or other reporter molecules. Other modifications have been made to the ribose phosphate backbone to increase the resistance to nucleases. These modifications include use of linkages such as methyl phosphonates, phosphorothioates and phosphorodithioates, and 2'-O-methyl ribose sugar moieties. Other oligonucleotide modifications include those made to modulate uptake and cellular distribution. Phosphorothioate oligonucleotides are presently being used as antisense agents in human clinical trials for the treatment of various disease states. Although some improvements in diagnostic and therapeutic uses have been realized with these oligonucleotide modifications, there exists an ongoing demand for improved oligonucleotide analogs.

There are several known nucleic acid analogs having nucleobases bound to backbones other than the naturally-occurring ribonucleic acids or deoxyribonucleic acids. These nucleic acid analogs have the ability to bind to nucleic acids with complementary nucleobase sequences. Among these, the peptide nucleic acids (PNAs), as described, for example, in WO 92/20702, have been shown to be useful as therapeutic and diagnostic reagents. This may be due to their generally higher affinity for complementary nucleobase sequence than the corresponding wild-type nucleic acids.

PNAs are useful surrogates for oligonucleotides in binding to DNA and RNA. Egholm et al., *Nature,* 1993, 365, 566, and references cited therein. The current literature reflects the various applications of PNAs. Hyrup et al., *Bioorganic & Med. Chem.,* 1996, 4, 5; and Nielsen, *Perspectives Drug Disc. Des.,* 1996, 4, 76.

PNAs are compounds that are analogous to oligonucleotides, but differ in composition. In PNAs, the deoxyribose backbone of oligonucleotide is replaced by a peptide backbone. Each subunit of the peptide backbone is attached to a naturally-occurring or non-naturally-occurring nucleobase. One such peptide backbone is constructed of repeating units of N-(2-aminoethyl)glycine linked through amide bonds. The synthesis of PNAs via preformed monomers was previously described in WO 92/20702 and WO 92/20703, the contents of which are herein incorporated by reference. More recent advances in the structure and synthesis of PNAs are illustrated in WO 93/12129 and U.S. Pat. No. 5,539,082, issued Jul. 23, 1996, the contents of both being herein incorporated by reference. Further, the literature is replete with publications describing synthetic procedures, biological properties and uses of PNAs. For example, PNAs possess the ability to effect strand displacement of double-stranded DNA. Patel, *Nature,* 1993, 365, 490. Improved synthetic procedures for PNAs have also been described. Nielsen et al., *Science,* 1991, 254, 1497; and Egholm, *J. Am. Chem. Soc.,* 1992, 114, 1895. PNAs form duplexes and triplexes with complementary DNA or RNA. Knudson et al., *Nucleic Acids Research,* 1996, 24, 494; Nielsen et al., *J. Am. Chem. Soc.,* 1996, 118, 2287; Egholm et al., *Science,* 1991, 254, 1497; Egholm et al., *J. Am. Chem. Soc.,* 1992, 114, 1895; and Egholm et al., *J Am. Chem. Soc.,* 1992, 114, 9677.

PNAs bind to both DNA and RNA and form PNA/DNA or PNA/RNA duplexes. The resulting PNA/DNA or PNA/RNA duplexes are bound tighter than corresponding DNA/DNA or DNA/RNA duplexes as evidenced by their higher melting temperatures ($T_m$). This high thermal stability of PNA/DNA(RNA) duplexes has been attributed to the neutrality of the PNA backbone, which results elimination of charge repulsion that is present in DNA/DNA or RNA/RNA duplexes. Another advantage of PNA/DNA(RNA) duplexes is that $T_m$ is practically independent of salt concentration. DNA/DNA duplexes, on the other hand, are highly dependent on the ionic strength.

Triplex formation by oligonucleotides has been an area of intense investigation since sequence-specific cleavage of double-stranded deoxyribonucleic acid (DNA) was demonstrated. Moser et al., *Science,* 1987, 238, 645. The potential use of triplex-forming oligonucleotides in gene therapy, diagnostic probing, and other biomedical applications has generated considerable interest. Uhlmann et al., *Chemical Reviews,* 1990, 90, 543. Pyrimidine oligonucleotides have been shown to form triple helix structures through binding to homopurine targets in double-stranded DNA. In these structures the new pyrimidine strand is oriented parallel to the purine Watson-Crick strand in the major groove of the DNA and binds through sequence-specific Hoogsteen hydrogen bonding. The sequence specificity is derived from thymine recognzig adenine (T:A-T) and protonated cytosine recognizing guanine (C+:G-C). Best et al., *J. Am. Chem. Soc.*, 1995, 117, 1187. In a less well-studied triplex motif, purine-rich oligonucleotides bind to purine targets of double-stranded DNA. The orientation of the third strand in this motif is anti-parallel to the purine Watson-Crick strand, and the specificity is derived from guanine recognizing guanine (G:G-C) and thymine or adenine recognizing adenine (A:A-T or T:A-T). Greenberg et al., *J. Am. Chem. Soc.*, 1995, 117, 5016.

Homopyrimidine PNAs have been shown to bind complementary DNA or RNA forming (PNA)$_2$/DNA(RNA) triplexes of high thermal stability. Egholm et al., *Science*, 1991, 254, 1497; Eghohm et al., *J. Am. Chem. Soc.*, 1992, 114, 1895; Egholm et al., *J Am. Chem. Soc.*, 1992, 114, 9677. The formation of triplexes involving two PNA strands and one nucleotide strand has been reported in U.S. patent application Ser. No. 08/088,661, filed Jul. 2, 1993, the contents of which are incorporated herein by reference. The formation of triplexes in which the Hoogsteen strand is parallel to the DNA purine target strand is preferred to formation of anti-parallel complexes. This allows for the use of bis-PNAs to obtain triple helix structures with increased pH-independent thermal stability using pseudoisocytosine instead of cytosine in the Hoogsteen strand. Egholm et al., *J Am. Chem. Soc.*, 1992, 114, 1895. Further, see WO 96/02558, the contents of which are incorporated herein by reference.

Peptide nucleic acids have been shown to have higher binding affinities (as determined by their Tm's) for both DNA and RNA than that of DNA or RNA to either DNA or RNA. This increase in binding affinity makes these peptide nucleic acid oligomers especially useful as molecular probes and diagnostic agents for nucleic acid species.

In addition to increased affinity, PNAs have increased specificity for DNA binding. Thus, a PNA/DNA duplex mismatch show 8 to 20° C. drop in the T$_m$ relative to the DNA/DNA duplex This decrease in T$_m$ is not observed with the corresponding DNA/DNA duplex mismatch. Egholm et al., *Nature* 1993, 365, 566.

A further advantage of PNAs, compared to oligonucleotides, is that the polyamide backbone of PNAs is resistant to degradation by enzymes.

Considerable research is being directed to the application of oligonucleotides and oligonucleotide analogs that bind to complementary DNA and RNA strands for use as diagnostics, research reagents and potential therapeutics. For many applications, the oligonucleotides and oligonucleotide analogs must be transported across cell membranes or taken up by cells to express their activity.

PCT/EP/01219 describes novel PNAs which bind to complementary DNA and RNA more tightly than the corresponding DNA. It is desirable to append groups to these PNAs which will modulate their activity, modify their membrane permeability or increase their cellular uptake property. One method for increasing amount of cellular uptake property of PNAs is to attach a lipophilic group. U.S. application Ser. No. 117,363, filed Sept. 3, 1993, describes several alkylamino functionalities and their use in the attachment of such pendant groups to oligonucleosides.

U.S. application Ser. No. 07/943,516, filed Sep. 11, 1992, and its corresponding published PCT application WO 94/06815, describe other novel amine-containing compounds and their incorporation into oligonucleotides for, inter alia, the purposes of enhancing cellular uptake, increasing lipophilicity, causing greater cellular retention and increasing the distribution of the compound within the cell.

U.S. application Ser. No. 08/116,801, filed Sep. 3, 1993, describes nucleosides and oligonucleosides derivatized to include a thiolalkyl functionality, through which pendant groups are attached.

Recently, liposomal drug-delivery systems incorporating various biomolecules and drugs have been studied and found to exhibit reduced toxicities and increased efficacy due to enhanced cellular uptake and distribution. Chonn and Cullis, *Current Opinion in Biotechnology*, 1995, 6, 698; Mannino et al., *Biotechniques*, 1988, 6, 682; Blume and Cevc, *Biochem et Biophys. Acta*, 1990,1029, 91; and Lappalainen et al., *Antiviral Res.*, 1994, 23, 119. Liposomes are microscopic spheres composed of an aqueous core and a lipid bilayer enveloping the core. Procedures for preparation of liposomes are available in the literature. G. Gregoridadis in "Liposome Technology," volume 2, G. Gregoridadis (ed.), CRC Press, 1993, p.1; Watwe and Bellare, *Curr. Sci.*, 1995, 68, 715. Several liposomal drugs are currently on the market or under development. Chonn and Cullis, *Current Opinion in Biotechnology*, 1995, 6, 698.

WO 96/10391, published Apr. 11, 1995, describes polyethylene glycol-modified ceramide lipids which are used to form liposomes, and the use of these liposomes as drug-delivery vehicles.

WO 96/24334, published Aug. 15, 1996, describes lipid constructs having an aminomannose-derivatized cholesterol moiety for the delivery of drugs to the cytoplasm of cells, particularly to vascular smooth muscle tissues.

WO 96/40627, published Dec. 19, 1996, describes cationic lipid-containing liposome formulations which are useful in the delivery of biomolecules such as oligonucleotides, nucleic acids, peptides and other agents.

Despite recent advances, there remains a need for stable compositions with enhanced cellular uptake and distribution.

SUMMARY OF THE INVENTION

The present invention provides peptide nucleic acids (PNAs) conjugated to a lipophilic group and having a modified backbone wherein an amino acid side chain is attached to the backbone. The present invention also provides liposomal compositions comprising a peptide nucleic acid (PNA) conjugated to a lipophilic group which is incorporated into liposomes. The PNAs of the present invention comprise nucleobases covalently bound to a polyamide backbone. Representative nucleobases include the four major naturally-occurring DNA nucleobases (i.e., thymine, cytosine, adenine and guanine), other naturally-occurring nucleobases (e.g. inosine, uracil, 5-methylcytosine, thiouracil and 2,6-diaminopurine) and artificial nucleobases (e.g., bromothymine, azaadenines and azaguanines). These nucleobases are attached to a polyamide backbone through a suitable linker.

Preferred peptide nucleic acids of the invention have the general formula (I):

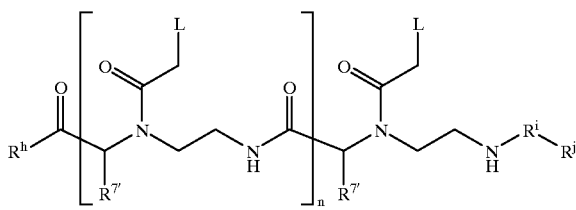

wherein:
   each L is, independently, a naturally-occurring nucleobase or a non-naturally-occuring nucleobase;
   each $R^{7'}$ is hydrogen or the side chain of a naturally-occurring or non-naturally-occurring amino acid, at least one $R^{7'}$ being the side chain of an amino acid;
   $R^h$ is OH, $NH_2$, or $NHLysNH_2$;
   each of $R^i$ and $R^j$ is, independently, a lipophilic group or an amino acid labeled with a fluorescent group; or $R^i$ and $R^j$, together, are a lipophilic group;
   n is an integer from 1 to 30.

PNAs having formula (I) wherein $R^i$ is D-lysine labeled with a fluorescent group and $R^j$ is an adamantoyl group are preferred. Even more preferred are PNAs of formula (I) wherein $R^i$ is D-lysine labeled with fluorescein and $R^j$ is an adamantoyl group. Also preferred are PNAs having formula (I) wherein $R^i$ and $R^j$, together, are an adamantoyl group. Further preferred are PNAs of formula (I) wherein at least one of said $R^{7'}$ is the side chain of D-lysine.

Preferably, the carbon atom to which substituent $R^{7'}$ is attached is stereochemically enriched. Hereinafter, "stereochemically enriched" means that one stereoisomer predominates over the other stereoisomer in a sufficient amount as to provide a beneficial effect. Preferably, one stereoisomer predominates by more than 50%. More preferably, one stereoisomer predominates by more than 80%. Even more preferably, one stereoisomer predominates by more than 90%. Still more preferably, one stereoisomer predominates by more than 95%. Even more preferably, one stereoisomer predominates by more than 99%. Still even more preferably, one stereoisomer is present substantially quantitatively.

The present invention also provides liposomal compositions comprising a peptide nucleic acid incorporated in a liposome, said peptide nucleic acid having formula (I) wherein:
   each L is, independently, a naturally-occurring nucleobase or a non-naturally-occurring nucleobase;
   each $R^{7'}$ is hydrogen or the side chain of a naturally-occurring or non-naturally-occuring amino acid;
   $R^h$ is OH, $NH_2$, or $NHLysNH_2$;
   each of $R^i$ and $R^j$ is, independently, a lipophilic group or an amino acid labeled with a fluorescent group; or $R^i$ and $R^j$, together, are a lipophilic group;
   n is an integer from 1 to 30.

PNAs having formula (I) wherein $R^i$ is D-lysine labeled with a fluorescent group and $R^j$ is an adamantoyl group are preferred. Even more preferred are PNAs of formula (I) wherein $R^i$ is D-lysine labeled with fluorescein and $R^j$ is an adamantoyl group. Also preferred are PNAs having formula (I) wherein $R^i$ and $R^j$, together, are an adamantoyl group. Further preferred are PNAs of formula (I) wherein at least one of said $R^{7'}$ is the side chain of D-lysine.

Preferably, the carbon atom to which substituent $R^{7'}$ is attached is stereochemically enriched.

The PNAs of the present invention are synthesized by adaptation of standard peptide synthesis procedures, either in solution or on a solid phase.

The present invention further provides methods for enhancing the cellular uptake and distribution of peptide nucleic acids by incorporation of amino acid side chains into PNA backbones, conjugating lipophilic groups with PNAs and introducing PNAs into liposomes.

DETAILED DESCRIPTION OF THE INVENTION

Figure 1:
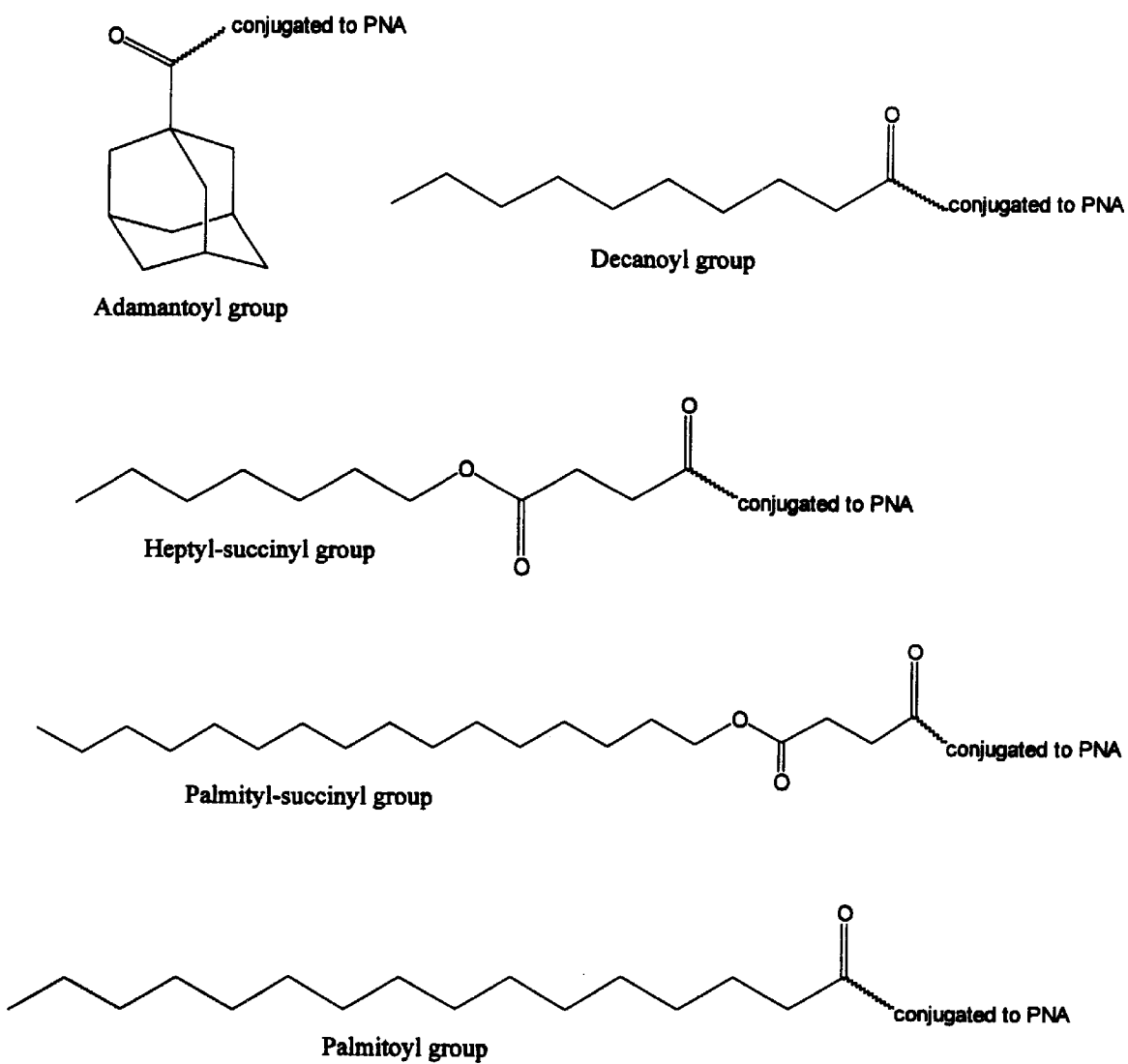
FIG. 1 shows structures of some lipophilic groups.

In accordance with the present invention, peptide nucleic acids and liposomal compositions exhibiting enhanced cellular uptake and distribution are provided. The peptide nucleic acids (PNAs) of the invention are assembled from a plurality of nucleobases which are attached to a polyamide backbone by a suitable linker. In one preferred embodiment of the present invention, the PNAs are conjugated to a lipophilic group. As used herein, "conjugating" refers to attaching a lipophilic group to a PNA of the invention. In another preferred embodiment, the polyamide backbone of PNAs of the invention is derivatized. As used herein, "derivatizing" refers to modifying the backbone of a PNA by attaching the side chain of at least one naturally-occurring or non-naturally-occurring amino acid to the polyamide backbone. The liposomal compositions of the present invention comprise peptide nucleic acids of the invention that are incorporated into liposomes. Thus, the liposomal compositions of the present invention comprise PNAs which are encapsulated by liposomes. The PNAs and liposomal compositions of the present invention exhibit enhanced cellular uptake and distribution.

The PNAs of the present invention have the formula (I) wherein nucleobase L is a naturally-occurring nucleobase attached at the position found in nature, i.e., position 9 for adenine or guanine, and position 1 for thymine or cytosine, a non-naturally-occurring nucleobase (nucleobase analog) or a nucleobase-binding moiety. Representative nucleobases include the four major naturally-occurring DNA nucleobases (i.e., thymine, cytosine, adenine and guanine), other naturally-occurring nucleobases (e.g. inosine, uracil, 5-methylcytosine, thiouracil and 2,6-diaminopurine) and artificial nucleobases (e.g., bromothymine, azaadenines and azaguanines). These nucleobases are attached to a polyamide backbone through a suitable linker.

The PNAs of formula (I) include one or more amino acid moieties within their structure. These amino acids may be naturally-occurring or non-naturally-occurring. Naturally-occurring amino acids include α-amino acids where the chiral center has a D-configuration. Such naturally-occurring amino-acids may be either essential or non-essential amino acids. Non-naturally-occurring amino acids used in the PNAs of the present invention of formula (I) include α-amino acids with chiral centers bearing an L-configuration. Non-naturally-occurring amino acids also include amino acids bearing unusual side chains that do not exist in nature and are prepared synthetically, such as halo- and cyano-substituted benzyl, tetrahydroisoquinolylmethyl, cyclohexylmethyl, and pyridylmethyl. Other synthetic amino-acids include β-amino acids.

The amino acids may be introduced into the PNAs of formula (I) either as part of the monomer used or at the terminal ends of the PNA. Any of the abovementioned amino acids could be incorporated into the monomeric building blocks used in PNA synthesis. Preferably the amino acid used is glycine, where $R^{7'}$ is H. $R^{7'}$ can also be methyl, ethyl, benzyl, isopropyl, p-hydroxybenzyl, halobenzyl, carboxymethyl, tetrahydroisoquinolinylmethyl, or aminohexanoyl. Amino acids may also be attached at the C-terminus of PNAs such that the terminal $R^h$—CO— group represents an amino acyl group derived from any naturally- or non-naturally-occurring amino acid, α- or β-amino acid, and with a D- or L-configuration at the α-chiral center. Preferably the C-terminal amino acid is lysine. Amino acids may also be incorporated at the N-terminal end of the PNA of structure (I) where each of $R^i$ and $R^j$ may, independently, be an amino acyl group derived from any naturally- or non-naturally-occurring amino acid, α- or p-amino acid, and with a D- or L-configuration at the α-chiral center. Preferably the N-terminal amino acid is lysine.

Lipophilic groups attached to PNA's of formula (I) of the present inventions include natural and synthetic fatty acids, fatty alcohol derivatives and diacylglycerol derivatives such as adipic acid, palmitic acid, decanoic acid, octadecanoic acid, oleic acid, elaidic acid, linoleic acid, bile acids, heptylsuccinic acid, palmitylsuccinic acid, polyglycolic acid, dioctadecylglycerol phosphatidic acid, dioleoylglycerol phosphatidic acid, adamantoyl, octadecyloxycarbonyl, and decalinoyl. These lipophilic groups may be attached at any suitable location in the PNA molecule of formula (I). Preferably, the lipophilic group is attached to the N-terminus of the PNA of the invention wherein each of $R^i$ and $R^j$ may, independently, be a lipophilic group. More preferably, $R^i$ and $R^j$, together, are an adamantoyl group.

The PNAs of the present invention have the formula (I) wherein labels, such as fluorescent groups, are incorporated so as to allow a convenient means by which to detect the PNA. Fluorescent groups include, but are not limited to, dyes such as fluorescein, rhodamine, pyrenyl, cyanine dyes, Cy5™ (Biological Detection Systems, Inc., Pittsburgh, Pa.), and derivatives of such dyes. These may be incorporated into the PNA of formula (I) at any suitable position in the PNA. Preferably, each of $R^i$ is a chemical moiety to which is attached a fluorescent group. It is more preferred that $R^i$ is an amino acid that has been derivatized with a fluorescent group. It is further more preferred that $R^i$ is a lysine with an ε-fluoresceinyl group.

Liposomal compositions of the invention comprise PNAs of the invention which are incorporated into liposomes. The liposomal compositions exhibit enhanced cellular uptake and distribution. Liposomes are a colloidal dispersion system, and constitute a stable delivery system which protects the incorporated PNA from the environment while being transported to target areas. Liposomes represent a stable delivery vehicle to enhance the in vitro and in vivo stability of the PNAs of the invention. The liposomal compositions of the present invention, comprising PNAs of the invention incorporated into liposomes, can be formulated as pharmaceutical compositions according to standard techniques known by the art-skilled using suitable and acceptable carriers and adjuvants.

Liposomes that may be used include small unilamellar vesicles (SUVs), large unilamellar vesicles (LUVs) and multilamellar vesicles (MLVs). It has been shown that LUVs, which range in size from 0.2–0.4 μm, can encapsulate a substantial percentage of an aqueous buffer containing large macromolecules (e.g., RNA, DNA and intact virions can be encapsulated within the aqueous interior and delivered to brain cells in a biologically active form: Fraley et al., *Trends Biochem. Sci.*, 1981, 6, 77). The composition of the liposome is usually a combination of lipids, particularly phospholipids, in particular, high phase transition temperature phospholipids, usually in combination with one or more steroids, particularly cholesterol. Examples of lipids useful in liposome production include phosphatidyl compounds, such as phosphatidylglycerol, phosphatidylcholine, phosphatidylserine, phosphatidylethanolamine, sphingolipids, cerebrosides and gangliosides. Particularly useful are diacyl phosphatidylglycerols, where the lipid moiety contains from 14–18 carbon atoms, particularly from 16–18 carbon atoms, and is saturated (lacking double bonds within the 14–18 carbon atom chain). Illustrative phospholipids include phosphatidylcholine, dipalmitoylphosphatidylcholine and distearoylphosphatidylcholine.

The targeting of liposomes can be either passive or active. Passive targeting utilizes the natural tendency of liposomes to distribute to cells of the reticuloendothelial system in organs that contain sinusoidal capillaries. Active targeting, by contrast, involves modification of the liposome by coupling thereto a specific ligand such as a viral protein coat (Morishita et al., *Proc. Natl. Acad. Sci. U.S.A.*, 1993, 90, 8474), monoclonal antibody (or a suitable binding portion thereof), sugar, glycolipid or protein (or a suitable oligopeptide fragment thereof), or by changing the composition and/or size of the liposome in order to achieve distribution to organs and cell types other than the naturally occurring sites of localization. The surface of the targeted colloidal dispersion system can be modified in a variety of ways. In the case of a liposomal targeted delivery system, lipid groups can be incorporated into the lipid bilayer of the liposome in order to maintain the targeting ligand in close association with the lipid bilayer. Various linking groups can be used for joining the lipid chains to the targeting ligand. The targeting ligand, which binds a specific cell surface molecule found predominantly on cells to which delivery of the oligonucleotides of the invention is desired, may be, for example, (1) a hormone, growth factor or a suitable oligopeptide fragment thereof which is bound by a specific cellular receptor predominantly expressed by cells to which delivery is desired; or (2) a polyclonal or monoclonal antibody, or a suitable fragment thereof (e.g., Fab; F(ab')$_2$) which specifically binds an antigenic epitope found predominantly on targeted cells. Two or more bioactive agents (e.g., a PNA and a conventional drug, or two PNAs) can be combined within, and delivered by, a single liposome. It is also possible to add agents to colloidal dispersion systems which enhance the intercellular stability and/or targeting of the contents thereof The PNAs of the present invention may be used for gene modulation (e.g., gene targeted drugs), diagnostics, biotechnology and other research purposes. The PNAs may also be used to target RNA and single-stranded DNA (ssDNA) to produce both antisense-type gene regulating moieties and as hybridization probes, e.g., for the identification and purification of nucleic acids. Furthermore, the PNAs may be modified in such a way that they form triple helices with double stranded DNA (dsDNA). Compounds that bind sequence-specifically to dsDNA have applications as gene targeted drugs. These compounds are extremely useful drugs for treating various diseases, including cancer, acquired immune deficiency syndrome (AIDS) and other virus infections and genetic disorders. Furthermore, these compounds may be used in research, diagnostics and for detection and isolation of specific nucleic acids.

Gene-targeted drugs are designed with a nucleobase sequence (preferably containing 10–20 units) complementary to the regulatory region (the promoter) of the target gene. Therefore, upon administration, the gene-targeted drugs bind to the promoter and prevent RNA polymerase from accessing the promoter. Consequently, no mRNA, and thus no gene product (protein), is produced. If the target is within a vital gene for a virus, no viable virus particles will be produced. Alternatively, the target region could be downstream from the promoter, causing the RNA polymerase to terminate at this position, thus forming a truncated mRNA/protein which is nonfunctional.

Synthesis of PNA Oligomers

The principle of anchoring molecules during a reaction onto a solid matrix is known as Solid Phase Synthesis or Merrifield Synthesis. Merrifield, *J. Am. Chem. Soc.*, 1963, 85, 2149; and *Science*, 1986, 232, 341. Established methods for the stepwise or fragment-wise solid phase assembly of amino acids into peptides normally employ a beaded matrix of cross-linked styrene-divinylbenzene copolymer. The cross-linked copolymer is formed by the pearl polymerization of styrene monomer to which is added a mixture of divinylbenzdnes. Usually, 1–2% cross-linking is employed. Such a matrix may be used in solid phase PNA synthesis of the present invention.

More than fifty methods for initial functionalization of the solid phase have been described in connection with traditional solid phase peptide synthesis. Barany and Merrifield in "The Peptides," Vol. 2, Academic Press, New York, 1979, pp. 1; and Stewart and Young in "Solid Phase Peptide Synthesis," 2nd ed., Pierce Chemical Company, Illinois, 1984. Regardless of its nature, the purpose of introducing a functionality on the solid phase is to form an anchoring linkage between the copolymer solid support and the C-terminus of the first amino acid to be coupled to the solid support. As will be recognized, anchoring linkages may also be formed between the solid support and the amino acid N-terminus. The "concentration" of a functional group present in the solid phase is generally expressed in millimoles per gram (mmol/g). All of these established methods are, in principle, useful within the context of the present invention.

A preferred method for PNA synthesis employs aminomethyl as the initial functionality. Aminomethyl is particularly advantageous as a "spacer" or "handle" group because it forms amide bonds with a carboxylic acid group in nearly quantitative amounts. A vast number of relevant spacer- or handle-forming bifunctional reagents have been described. Barany et al. *Int. J. Peptide Protein Res.*, 1987, 30, 705. Certain functionalities (e.g., benzhydrylamino, 4-methylbenzhydrylamino and 4-methoxybenzhydrylamino) which may be incorporated for the purpose of cleavage of a synthesized PNA chain from the solid support such that the C-terminal of the PNA chain is released as an amide, require no introduction of a spacer group. Any such functionality may advantageously be employed in the context of the present invention.

Exemplary N-protecting groups are tert-butyloxycarbonyl (BOC) (Carpino, *J. Am. Chem. Soc.*, 1957, 79, 4427; McKay, et al., *J. Am. Chem. Soc.*, 1957, 79, 4686; and Anderson et al., *J. Am. Chem. Soc.*, 1957, 79, 6180), 9-fluorenylmethyloxycarbonyl (FMOC) (Carpino et al., *J. Am. Chem. Soc.*, 1970, 92, 5748 and *J. Org. Chem.*, 1972, 37, 3404), Adoc (Hass et al., *J. Am. Chem. Soc.*, 1966, 88, 1988), Bpoc (Sieber *Helv. Chem. Acta.*, 1968, 51, 614), Mcb (Brady et al., *J. Org. Chem.*, 1977, 42, 143), Bic (Kemp et al., *Tetrahedron*, 1975,4624), o-nitrophenylsulfenyl Nps) (Zervas et al., *J. Am. Chem. Soc.*, 1963, 85, 3660) and dithiasuccinoyl (Dts) (Barany et al., *J. Am. Chem. Soc.*, 1977, 99, 7363), as well as other groups which are known to those skilled in the art. These amino-protecting groups, particularly those based on the widely-used urethane functionality, prohibit racemization (mediated by tautomerization of the readily formed oxazolinone (azlactone) intermediates (Goodman et al., *J. Am. Chem. Soc.*, 1964, 86, 2918)) during the coupling of most α-amino acids. In addition to such amino-protecting groups, nonurethane-tpe of amino-protecting groups are also applicable when assembling PNA molecules.

The choice of side chain protecting groups, in general, depends on the choice of the amino-protecting group, because the side chain protecting group must withstand the conditions of the repeated amino deprotection cycles. This is true whether the overall strategy for chemically assembling PNA molecules relies on, for example, different acid stability of amino and side chain protecting groups (such as is the case for the above-mentioned "BOC-benzyl" approach) or employs an orthogonal, that is, chemoselective, protection scheme (such as is the case for the above-mentioned "FMOC-t-Bu" approach).

Following coupling of the first amino acid, the next stage of solid phase synthesis is the systematic elaboration of the desired PNA chain. This elaboration involves repeated deprotection/coupling cycles. A temporary protecting group, such as BOC or FMOC, on the last coupled amino acid is quantitatively removed by a suitable treatment, for example, by acidolysis, such as with tifluoroacetic acid in the case of BOC, or by base treatment, such as with piperdine in the case of FMOC, so as to liberate the N-terminal amine function.

The next desired N-protected amino acid is then coupled to the N-terminal of the last coupled amino acid. This coupling of the C-terminal of an amino acid with the N-terminal of the last coupled amino acid can be achieved in several ways. For example, it can be achieved by providing the incoming amino acid in a form with the carboxyl group activated by any of several methods, include the initial formation of an active ester derivative such as a phthalimido ester (Nefkens et al., *J. Am. Chem. Soc.*, 1961, 83, 1263), a pentafluorophenyl ester (Kovacs et al., *J. Am. Chem. Soc.*, 1963, 85, 183), an imidazole ester (Li et al., *J. Am Chem. Soc.*, 1970, 92, 7608), and a 3-hydroxy-4-oxo-3,4-dihydroquinazoline (Dhbr-OH) ester (Konig et al., *Chem. Ber.*, 1973, 103, 2024 and 2034), or the initial formation of an anhydride such as a symmetrical anhydride (Wieland et al , *Angew. Chem., Int., Ed. Engl.*, 1971, 10, 336). Alternatively, the carboxyl group of the incoming amino acid can be reacted directly with the N-terminal of the last coupled amino acid with the assistance of a condensation reagent such as, for example, dicyclohexylcarbodiimide (Sheehan et al., *J. Am. Chem. Soc.*, 1955, 77, 1067) or derivatives thereof. Benzotriazoyl N-oxy-trisdimethylaminnophosphonium hexafluorophosphate (BOP), "Castro's reagent" (see Rivaille et al., *Tetrahedron*, 1980, 36,3413), is recommended when assembling PNA molecules comprising secondary amino groups.

Following the assembly of the desired PNA chain, including protecting groups, the next step will normally be deprotection of the amino acid moieties of the PNA chain and cleavage of the synthesized PNA from the solid support. These processes can take place substantially simultaneously, thereby providing the free PNA molecule in the desired form.

In the above-mentioned "BOC-benzyl" protection scheme, the final deprotection of side chains and release of the PNA molecule from the solid support is most often carried out by the use of strong acids such as anhydrous HF (Sakakibara et al., *Bull. Chem. Soc. Jpn.,* 1965, 38, 4921), boron tris (trifluoroacetate) (Pless et al., *Helv. Chim. Acta,* 1973, 46, 1609) and sulfonic acids, such as trifluoromethanesulfonic acid and methanesulfonic acid (Yajima et al., *J. Chem. Soc., Chem. Comm.,* 1974, 107). A strong acid (e.g., anhydrous HF) deprotection method may produce very reactive carbocations that may lead to alkylation and acylation of sensitive residues in the PNA chain. Such side reactions are only partly avoided by the presence of scavengers such as anisole, phenol, dimethyl sulfide, and mercaptoethanol. Thus, the sulfide-assisted acidolytic $S_N 2$ deprotection method (Tam et al., *J. Am. Chem. Soc.,* 1983, 105, 6442 and *J. Am. Chem. Soc., 1986, 108, 5242*), the so-called "low" method, which removes the precursors of harmful carbocations to form inert sulfonium salts, is frequently employed in peptide and PNA synthesis. Other methods for deprotection and/or final cleavage of the PNA-solid support bond may include base-catalyzed alcoholysis (Barton et al., *J. Am. Chem. Soc.,* 1973, 95, 4501), ammonolysis, hydrazinolysis (Bodanszky et al., *Chem. Ind.,* 1964 1423), hydrogenolysis (Jones, *Tetrahedron Lett.* 1977 2853 and Schlatter et al., *Tetrahedron Lett.* 1977 2861)) and photolysis (Rich and Gurwara, *J. Am. Chem. Soc.,* 1975 97, 1575)).

Finally, in contrast with the chemical synthesis of conventional peptides, stepwise chain building of achiral PNAs such as those based on aminoethylglycyl backbone units can start either from the N-terminus or the C-terminus. Those skilled in the art will recognize that synthesis commencing at the C-terminus typically employ protected amine groups and free or activated acid groups, and syntheses commencing at the N-terminus typically employ protected acid groups and free or activated amine groups.

Likely therapeutic and prophylactic targets include herpes simplex virus (HSV), human papillomavirus (HPV), human immunodeficiency virus (HIV), candida albicans, influenza virus, cytomegalovirus (CMV), intercellular adhesion molecules (ICAM), 5-lipoxygenase (5-LO), phospholipase $A_2$ ($PLA_2$), protein kinase C (PKC), and the ras oncogene. Potential treatment of such targeting include ocular, labial, genital, and systemic herpes simplex I and II infections; genital warts; cervical cancer; common warts; Kaposi's sarcoma; AIDS; skin and systemic fungal infections; flu; pneumonia; retinitis and pneumonitis in immunosuppressed patients; mononucleosis; ocular, skin and systemic inflammation; cardiovascular disease; cancer; asthma; psoriasis; cardiovascular collapse; cardiac infarction; gastrointestinal disease; kidney disease; rheumatoid arthritis; osteoarthritis; acute pancreatitis; septic shock; and Crohn's disease.

In general, for therapeutic or prophylactic treatment, a patient suspected of requiring such therapy is administered a PNA or liposomal composition of the present invention, commonly in a pharmaceutically acceptable carrier, in amounts and for periods of time which will vary depending upon the nature of the particular disease, its severity and the patient's overall condition. The PNAs and liposomal compositions of the invention can be formulated in a pharmaceutical composition, which may include carriers, thickeners, diluents, buffers, preservatives, surface active agents and the like. Pharmaceutical compositions may also include one or more active ingredients such as antimicrobial agents, anti-inflammatory agents, anesthetics and the like, in addition to the peptide nucleic acids.

The pharmaceutical composition may be administered in a number of ways depending upon whether local or systemic treatment is desired, and upon the area to be treated. Administration may be topical (including ophthalmic, vaginal, rectal, intranasal, transdermal), oral or parenteral, for example, by intravenous drip, subcutaneous, intraperitoneal or intramuscular injection or intrathecal or intraventricular administration.

Formulations for topical administration may include transdermal patches, ointments, lotions, creams, gels, drops, suppositories, sprays, liquids and powders. Conventional pharmaceutical carriers, nucleic acid carriers, aqueous, powder or oily bases, thickeners and the like may be necessary or desirable in certain circumstances. Coated condoms, gloves and the like may also be useful. Topical administration also includes delivery of the PNAs and liposomal compositions of the invention into the epidermis of an animal by electroporation. Zewart et al,. WO 96/39531, published Dec. 12, 1996.

Compositions for oral administration include powders or granules, suspensions or solutions in aqueous or non-aqueous media, capsules, sachets, or tablets. Thickeners, flavorings, diluents, emulsifiers, dispersing aids or binders may be desirable.

Intravitreal injection, for direct delivery of the PNAs and liposomal compositions of the invention to the vitreous humor of the eye of an animal is described in U.S. Pat. No. 5,595,978, issued Jan. 21, 1997, the contents of which are herein incorporated by reference.

Intraluminal administration, for direct delivery of PNAs and liposomal compositions of the invention to an isolated portion of a tubular organ or tissue (e.g., artery, vein, ureter or urethra) may be desired for the treatment of patients with diseases or conditions afflicting the lumen of such organs or tissues. To effect this mode of administration, a catheter or cannula is surgically introduced by appropriate means. After isolation of the portion of the tubular organ or tissue for which treatment is sought, the PNA or liposomal composition of the invention is infused through the catheter or cannula. The infusion catheter or cannula is then removed, and flow within the tubular organ or tissue is restored by removal of the ligatures which effected the isolation of a segment thereof. Morishita et al., *Proc. Natl. Acad. Sci, U.S.A.,* 1993, 90, 8474.

Intraventricular administration, for direct delivery of PNAs or liposomal compositions of the invention to the brain of a patient, may be desired for the treatment of patients with diseases or conditions afflicting the brain. To effect this mode of administration, a silicon catheter is surgically introduced into a ventricle of the brain, and is connected to a subcutaneous infusion pump (Medtronic, Inc., Minneapolis, Minn.) that has been surgically implanted in the abdominal region. Zimm et al., *Cancer Research,* 1984, 44, 1698; and Shaw, *Cancer,* 1993, 72(11 Suppl.), 3416. The pump is used to inject the PNA or liposomal composition, and allows precise dosage adjustments and variation in dosage schedules with the aid of an external programming device. The reservoir capacity of the pump is 18–20 mL, and infusion rates may range from 0.1 mL/hour to 1 mL/hour. Depending on the frequency of administration, ranging from daily to monthly, and the dose to be administered, ranging from 0.01 µg to 100 g per kg of body weight, the pump reservoir may be refilled at 3–10 week intervals. Refilling of the pump is accomplished by percutaneous puncture of the self-sealing septum of the pump. Compositions for intraventricular administration may include sterile aqueous solutions which may also contain buffers, diluents and other suitable additives.

Intrathecal administration, for the direct delivery of PNAs or liposomal compositions of the invention into the spinal column of a patient, may be desired for the treatment of patients with diseases of the central nervous system. To effect this route of administration, a silicon catheter is surgically implanted into the L3-4 lumbar spinal interspace of the patient, and is connected to a subcutaneous infusion pump which has been surgically implanted in the upper abdominal region. Luer and Hatton, *The Annals of Pharmacotherapy*, 1993, 27, 912; Ettinger et al., *Cancer*, 1978, 41, 1270; and Yaida et al., *Regul. Pept.*, 1995, 59, 193. The pump is used to inject the PNA or liposomal composition, and allows precise dosage adjustments and variations in dose schedules with the aid of an external programming device. The reservoir capacity of the pump is 18–20 mL, and infusion rates may vary from 0.1 mL/hour to 1 mL/hour. Depending on the frequency of administration, ranging from daily to monthly, and dosage to be administered, ranging from 0.01 µg to 100 g per kg of body weight, the pump reservoir may be refilled at 3–10 week intervals. Refilling of the pump is accomplished by a single percutaneous puncture to the self-sealing septum of the pump. Compositions for intrathecal administration may include sterile aqueous solutions which may also contain buffers, diluents and other suitable additives.

To effect delivery to areas other than the brain or spinal column via this method, the silicon catheter may be configured to connect the subcutaneous infusion pump to, e.g., the hepatic artery, for delivery to the liver. Kemeny et al., *Cancer*, 1993, 71, 1964. Infusion pumps may also be used to effect systemic delivery. Ewel et al., *Cancer Research*, 1992, 52, 3005; and Rubenstein et al., *J Surg. Oncol.*, 1996, 62, 194.

Compositions for parenteral, intrathecal or intraventricular administration, or liposomal systems, may include sterile aqueous solutions which may also contain buffers, diluents and other suitable additives. Dosing is dependent on severity and responsiveness of the disease state to be treated, with the course of treatment lasting from several days to several months, or until a care is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual PNAs, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years.

Synthesis of Monomer Subunits

The monomer subunits preferably are synthesized by a general scheme that commences with the preparation of either the methyl or ethyl ester of (BOC-aminoethyl)glycine, via a protection/deprotection procedure, as described in Examples 1 and 2. The synthesis of thymine monomer is described in Examples 4 and 5, and the synthesis of protected cytosine monomer its described in Example 6.

The synthesis of a protected adenine monomer involves alkylation of adenine with ethyl bromoacetate (Example 7) and verification of the position of substitution (i.e. position 9) by X-ray crystallography. The $N^6$-amino group is then protected with the benzyloxycarbonyl group by the use of the reagent N-ethyl-benzyloxycarbonylimidazole tetrafluoroborate (Example 8). Simple hydrolysis of the product ester (Example 9) gave $N^6$-benzyloxycarbonyl-9-carboxymethyl adenine (Examples 10 and 11), which was used in the standard PNA oligomer synthesis.

For the synthesis of the protected G-monomer, the starting material, 2-amino-6-chloropurine, was alkylated with bromoacetic acid (Example 12), and the 6-chloro group was then substituted with a benzyloxy group (Example 13). The resulting acid was coupled to the (BOC-aminoethyl)glycine methyl ester (from Example 2) with agent PyBrop™ being used as a coupling agent, and the resulting ester was hydrolyzed (Example 14) to afford the protected G monomer. The $O^6$-benzyl group was removed in the final HF-cleavage step following synthesis of the PNA-oligomer.

Additional objects, advantages, and novel features of the present invention will become apparent to those skilled in the art upon examination of the following examples thereof. The following examples illustrate the invention and are not intended to limit the same. Those skilled in the art will recognize, or be able to ascertain through routine experimentation, numerous equivalents to the specific substances, compositions, and procedures described herein. Such equivalents are considered to be within the scope of the present invention.

General Remarks

The following abbreviations are used in the experimental examples: DMF, N,N-dimethylformamide; Tyr, tyrosine; Lys, lysine; DCC, N,N-dicyclohexyl-carbodiimide; DCU, N,N-dicyclohexylurea; THF, tetrahydrofuran; aeg, N-acetyl-N-(2'-aminoethyl)glycine; aek, N-acetyl-N-(2'-aminoethyl)lysine; Pfp, pentafluorophenyl; BOC, tert-butoxycarbonyl; Z, benzyloxycarbonyl; NMR, nuclear magnetic resonance; s, singlet; d, doublet; dd, doublet of doublets; t; triplet; q, quartet; m, multiplet; b, broad; δ, chemical shift; ppm, parts per million (chemical shift).

NMR spectra were recorded on JEOL FX 90Q spectrometer or a Bruker 250 MHz with tetramethylsilane as an internal standard. Mass spectrometry was performed on a MassLab VG 12–250 quadropole instrument fitted with a VG FAB source and probe. Melting points were recorded on a Buchi melting point apparatus and are uncorrected. N,N-Dimethylformamide was dried over 4 Å molecular sieves, distilled and stored over 4 Å molecular sieves. Pyridine (HPLC quality) was dried and stored over 4 Å molecular sieves. Other solvents used were either the highest quality obtainable or were distilled prior to use. Dioxane was passed through basic alumina prior to use. BOC-anhydride, 4-nitrophenol, methyl bromoacetate, benzyloxycarbonyl chloride, pentafluorophenol were all obtained from Aldrich Chemical Company. Thymine, cytosine, adenine were all obtained from Sigma.

Thin layer chromatography (tlc) was performed using the following solvent systems: (1) chloroform:triethyl amine:methanol, 7:1:2; (2) methylene chloride:methanol, 9:1; (3) chloroform:methanol:acetic acid 85:10:5. Spots were visualized by UV (254 nm) and/or spraying with a ninhydrin solution (3 g ninhydrin in 1000 mL of 1-butanol and 30 mL of acetic acid), after heating at 120° C. for 5 minutes and, after spraying, heating again.

The carboxyl terminal (C terminus) end of PNA oligomers can be substituted with a variety of functional groups. One way this is performed is through the use of different resnis. The amino terminal (N terminus) end of PNA oligomers can also be capped with a carboxylic acid-based capping reagent for the final PNA monomer in the final coupling step, or substituted with a variety of conjugate groups. Representative examples of the types of C and N terminal groups are shown below.

| Resin Employed | aeg-PNA/aeg-PNA Derivative Prepared |
|---|---|
| (Capping Reagent = Acetyl) | |
| Merrifield | $CH_3CONH$-(PNA)-COOH |
|  | $H_2N$-(PNA)-COOH |
| Lys Substituted Merifield | $H_2N$-(PNA)-Lys-COOH |
| Merrifield | $H_2N$-(PNA)-$CONH_2$ |
| Lys Substituted MBHA | $H_2N$-(PNA)-Lys-$CONH_2$ |
| Lys Substituted Merrifield | $CH_3CONH$-(PNA)-Lys-COOH |
|  | $H_2N$-(PNA)-COOH |
| Lys Substituted Merrifield | $H_2N$-(PNA)-Lys-COOH |
| Merrifield | $H_2N$-(PNA)-$CONH_2$ |
| MBHA | $H_2N$-(PNA)-$CONH_2$ |
| Lys Substituted MBHA | $H_2N$-(PNA)-Lys-$CONH_2$ |
| MBHA | $CH_3CONH$-(PNA)-$CONH_2$ |
|  | $H_2N$-(PNA)-$CONH_2$ |
| Lys Substituted MBHA | $CH_3CONH$-(PNA)-Lys-$CONH_2$ |
| (Capping Reagent = N-Boc glycine) | |
| Merrifield | BocGly-(PNA)-COOH |
| Lys Substituted Merrifield | BocGly-(PNA)-Lys-COOH |
| MBHA | BocGly-(PNA)-$CONH_2$ |
| Lys Substituted MBHA | BocGly-(PNA)-Lys-$CONH_2$ |
| (Capping Reagent = 1. Glycine; 2. Cholic Acid (Chol)) | |
| Merrifield | Chol-Gly-(PNA)-COOH |
| Lys Substituted Merrifield | Chol-Gly-(PNA)-Lys-COOH |
| MBHA | Chol-Gly-(PNA)-$CONH_2$ |
| Lys Substituted MBHA | Chol-Gly-(PNA)-Lys-$CONH_2$ |

Further examples are found in U.S. application Ser. No. 08/275,951, filed Jul. 15, 1994, and incorporated herein by reference.

EXAMPLE 1

Synthesis of N-benzyloxycarbonyl-N'-(BOC-aminoethyl)glycine

Aminoethyl glycine (52.86 g, 0.447 mol) was dissolved in water (900 mL) and dioxane (900 mL) was added. The pH was adjusted to 11.2 with 2N NaOH. While the pH was kept at 11.2, tert-butyl-p-nitrophenyl carbonate (128.4 g, 0.537 mol) was dissolved in dioxane (720 mL) and added dropwise over the course of 2 hours. The pH was kept at 11.2 for at least three more hours and then allowed to stand overnight, with stirring. The yellow solution was cooled to 0° C. and the pH was adjusted to 3.5 with 2 N HCl. The mixture was washed with chloroform (4×100 mL), and the pH of the aqueous phase was readjusted to 9.5 with 2 N NaOH at 0° C. Benzyloxycarbonyl chloride (73.5 m,L 0.515 mol) was added over half an hour, while the pH was kept at 9.5 with 2 N NaOH. The pH was adjusted frequently over the next 4 hours, and the solution was allowed to stand overnight, with stirring. On the following day the solution was washed with ether (3×600 mL) and the pH of the solution was afterwards adjusted to 1.5 with 2 N HCl at 0° C. The title compound was isolated by extraction with ethyl acetate (5×1000 mL). The ethyl acetate solution was dried over magnesium sulfate and evaporated to dryness, in vacuo. This afforded 138 g of the product, which was dissolved in ether (300 mL) and precipitated by the addition of petroleum ether (1800 mL). Yield 124.7 g (79%). M.p. 64.5–85 ° C. Anal. for $C_{17}H_{24}N_2O_6$ found(calc.) C, 58.40(57.94); H; 7.02(6.86); N, 7.94(7.95). 1H-NMR (250 MHz, $CDCl_3$) 7.33 & 7.32 (5H, Ph); 5.15 & 5.12 (2H, Ph$CH_2$); 4.03 & 4.01 (2H, N$CH_2CO_2$H); 3.46 (b, 2H, BOC—NH$CH_2CH_2$); 3.28 (b, 2H, $\overline{BOC}$—NH$CH_2CH_2$) 1.43 & 1.40 (9H, t-$\overline{Bu}$). HPLC (260 nm) 20.71 min. (80.2%) and 21.57 min. (19.8%). The UV-spectra (200 nm–300 nm) are identical, indicating that the minor peak consists of Bis-Z-AEG.

EXAMPLE 2

Synthesis of N'-BOC-aminoethylglycine Esters (a) Ethyl ester: N-Benzyloxycarbonyl-N'-(BOC-aminoethyl)glycine (60 g, 0.170 mol) and N,N-dimethyl-4aminopyridine (6 g) were dissolved in absolute ethanol (500 mL), and cooled to 0° C. before the addition of DCC (42.2 g, 0.204 mol). The ice bath was removed after 5 minutes and stirring was continued for 2 more hours. The precipitated DCU (32.5 g, dried) was removed by filtration and washed with ether (3×100 mL). The combined filtrate was washed successively with diluted potassium hydrogen sulfate (2×400 mL), diluted sodium hydrogencarbonate (2×400 mL) and saturated sodium chloride (1×400 mL). The organic phase was filtered, then dried over magnesium sulfate, and evaporated to dryness, in vacuo, which yielded 66.1 g of an oily substance which contained some DCU.

The oil was dissolved in absolute ethanol (600 mL) and was added 10% palladium on carbon (6.6 g) was added. The solution was hydrogenated at atmospheric pressure. After 4 hours, 3.3 L was consumed out of the theoretical 4.2 L. The reaction mixture was filtered through celite and evaporated to dryness, in vacuo, affording 39.5 g (94%) of an oily substance. A 13 g portion of the oily substance was purified by silica gel ($SiO_2$, 600 g) chromatography. After elution with 300 mL of 20% petroleum ether in methylene chloride, the title compound was eluted with 1700 mL of 5% methanol in methylene chloride. The solvent was removed from the fractions, in vacuo, to yield 8.49 g product of satisfactory purity. Alternatively 10 g of the crude material was purified by Kugelrohr distillation. $^1$H-NMR (250 MHz, $CD_3OD$); 4.77 (b. s, NH); 4.18 (q, 2H, Me$CH_2$—); 3.38 (s, 2H, NC $H_2CO_2Et$); 3.16 (t, 2H, BOC—NH$\overline{C}CH_2H_2$); 2.68 (t, 2H, $\overline{BOC}$—NH$CH_2CH_2$); 1.43 (s, 9H, t-$\overline{Bu}$) and 1.26 (t, 3H, $CH_3$) $^{13}$C-NMR 17$\overline{1}$.4 ($\underline{C}$OEt); 156.6 (CO); 78.3 (($CH_3)_3\underline{C}$); 59.9 ($CH_2$); 49.0 ($CH_2$); 48.1 ($CH_2$); 39.0 ($CH_2$); 26.9 ($CH_2$) and 12.6 ($CH_3$)

(b) Methyl ester: The above procedure for the ethyl ester was used, with methanol being substituted for ethanol. The final product was purified by column chromatography.

EXAMPLE 3

Alternate Large-scale Synthesis of (N'-BOC-aminoethyl)glycine Ethyl Ester (a) Preparation of BOC-aminoacetaldehyde 3-Amino-1,2-propanediol (80 g, 0.88 mol) was dissolved in water (1500 mL) and the solution was cooled to 4° C., after which BOC-anhydride (230 g, 1.05 mol) was added in one portion. The solution was gently heated to room temperature in a water bath. The pH was maintained at 10.5 by the dropwise addition of sodium hydroxide. Over the course of the reaction, a total of 70.2 g of NaOH, dissolved in 480 mL of water, was added. After stirring overnight, ethyl acetate (1000 mL) was added, the mixture cooled to 0° C. and the pH adjusted to 2.5 by the addition of 4 M hydrochloric acid. The ethyl acetate layer was removed and the acidic aqueous solution was extracted with more ethyl acetate (8×500 mL). The combined ethyl acetate solution was reduced to a volume of 1500 mL using a rotary evaporator. The resulting solution was washed with half saturated potassium hydrogen sulphate (1500 mL) and then with saturated sodium chloride. It then was dried over magnesium sulphate and evaporated to dryness, in vacuo. Yield: 145.3 g (86%).

3-BOC-amino-1,2-propanediol (144.7 g, 0.757 mol) was suspended in water (750 mL) and potassium periodate (191.5 g, 0.833 mol) was added. The mixture was stirred under nitrogen for 2.5 h and the precipitated potassium iodate was removed by filtration and washed once with water (100 mL). The aqueous phase was extracted with chloroform (6×400 mL). The chloroform extracts were dried and evaporated to dryness, in vacuo. Yield: 102 g (93%) of an oil. BOC-aminoacetaldehyde was purified by kugelrohr distillation at 84° C. and 0.3 mm Hg, in two portions. Yield: 79 g (77%) as a colorless oil.

(b) Preparation of (N'-BOC-aminoethyl)glycine Methyl Ester

Palladium on carbon (10%, 2.00 g) was added to a solution of BOC-aminoacetaldehyde (10 g, 68.9 mmol) in methanol (150 mL) at 0C. Sodium acetate (11.3 g, 138 mmol) in methanol (150 mL), and glycine methyl ester hydrochloride (8.65 g; 68.9 mmol) in methanol (75 mL) ware added. The, mixture was hydrogenated at atmospheric pressure for 2.5 h, then filtered through celite and evaporated to dryness, in vacua. The material was redissolved in water (150 mL) and the pH adjusted to 8 with 0.5 N NaOH. The aqueous solution was extracted with methylene chloride (5×150 mL). The combined extracts were dried over sodium sulphate and evaporated to dryness, in vacuo. This resulted in 14.1 g (88%) yield of (N'-BOC-aminoethyl)glycine methyl ester. The crude material was purified by kugelrohr destination at 120° C. and 0.5 mm Hg to give 11.3 g (70%) of a colorless oil. The product had a purity that was higher than the material produced in example 26 according to tic analysis (10% methanol in methylene chloride).

Alternatively, sodium cyanoborohydride can be used as reducing agent instead of hydrogen (with Pd(C) as catalyst), although the yield (42%) was lower.

(C) Preparation of (N'-BOC-aminoethyl)glycine Ethyl Ester

The title compound was prepared by the above procedure with glycine ethyl ester hydrochloride substituted for glycine methyl ester hydrochloride. Also, the solvent used was ethanol. The yield was 78%.

EXAMPLE 4

Synthesis of 1-(BOC-aeg)thymine Ethyl Ester

N'-BOC-aminoethylglycine ethyl ester (13.5 g, 54.8 mmol), DhbtOH (9.84 g, 60.3 mmol) and 1-carboxymethyl thymine (11.g, 60.3 mmol) were dissolved in DMF (210 mL). Methylene chloride (210 mL) was added. The solution was cooled to 0° C. in an ethanol/ice bath and DCC (13.6 g, 65.8 mmol) was added. The ice bath was removed after 1 hour and stirring was continued for another 2 hours at ambient temperature. The precipitated DCU was removed bad filtration and washed twice with methylene chloride (2×75 mL). To the combined filtrate was added more methylene chloride (650 mL). The solution was washed successively with diluted sodium hydrogen carbonate (3×500 mL), diluted potassium hydrogen sulfate (2×500 mL), and saturated sodium chloride (1×500 mL). Some of the precipitate was removed from the organic phase by filtration, The organic phase was dried over magnesium sulfate and evaporated to dryness, in vacuo. The oily residue was dissolved in methylene chloride (150 mL), filtered, and the title compound was precipitated by the addition of petroleum ether (350 mL) at 0° C. The methylene chloride/petroleum ether procedure was repeated once. This afforded 16 g (71%) of a material which was more than 99% pure by HPLC.

EXAMPLE 5

Synthesis of 1-(BOC-aeg)thymine

The material from Example 4 was suspended in THF (194 mL, gives a 0.2 M solution), and 1 M aqueous lithium hydroxide (116 mL) was added. The mixture was stirred for 45 minutes at ambient temperature and then filtered to remove residual DCU. Water (40 mL) was added to the solution which was then washed with methylene chloride (300 mL). Additional water (30 mL) was added, and the alkaline solution was washed once more with methylene chloride (150 mL). The aqueous solution was cooled to 0° C. and the pH was adjusted to 2 by the dropwise addition of 1 N HCl (approx. 110 mL). The title compound was extracted with ethyl acetate (9×200 mL), the combined extracts were dried over magnesium sulfate and were evaporated to dryness, in vacua. The residue was evaporated once from methanol, which after drying overnight afforded a colorless glassy solid. Yield: 9.57 g (64%). HPLC>98% $R_T$14.8 minutes. Anal. for $C_{16}H_{24}N_4O_7 \cdot 0.25$ $HH_2O$ Found (calc.) C, 49.29(49.42); H; 6.52(6.35); N, 14.11–14.41. Due to the limited rotation around the secondary amide, several of the signals were doubled in the ratio 2:1 (indicated in the list by mj. for major and mi. for minor). $^1$H-NMR (250 MHz, DMSO-$d_6$) δ: 12.75 (bs, 1H, $CO_2H$); 11.28 (s, 1H, mj, imide NH); 11.26 (s, 1H, mi, imide NH); 7.30 (s, 1H, mj, T H-6); 7.26 (s, 1H, mi, T H-6); 6.92 (bt, 1H, mj, BOC—NH); 6.73 (bt, 1H, mi, BOC—NH); 4.64 (s, 2H, mj, $CH_2CON$); 4.46 (s, 2H, mj, $CH_2CON$); 4.19 (s, 2H, mi, $CH_2CO_2H$); 3.97 (s,2H, mj, $CH_2CO_2H$); 3.63–3.01 (unresolved m, includes water, C $\underline{H_2CH_2}$); 1.75 (s, 3H, $CH_3$) and 1.38 (s, 9H, t-Bu).

EXAMPLE 6

Synthesis of $N^4$-benzyloxycarbonyl-1-(BOC-aeg) cytosine

N'-BOC-aminoethyl glycine ethyl ester (5 g, 20.3 mmol), DhbtOH (3.64 g, 22.3 mmol) and $N^4$-benzyloxycarbonyl-1-carboxymethyl cytosine (6.77 g, 22.3 mmol) were suspended in DMF (100 mL). Methylene chloride (100 mL) was added. The solution was cooled to 0° C. and DCC (5.03 g, 24.4 mmol) was added. The ice bath was removed after 2 h and stirring was continued for another hour at ambient temperature. The reaction mixture then was evaporated to dryness, in vacuo. The residue was suspended in ether (100 mL) and stirred vigorously for 30 minutes. The solid material was isolated by filtration and the ether wash procedure was repeated twice. The material was then stirred vigorously for 15 minutes with dilute sodium hydrogencarbonate (approx. 4% solution, 100 mL), filtered and washed with water. This procedure was then repeated once, which after drying left 17 g of yellowish solid material. The solid was then refluxed with dioxane (200 mL) and filtered while hot. After cooling, water (200 mL) was added. The precipitated material was isolated by filtration, washed with water, and dried. According to HPLC (observing at 260 nm) this material has a purity higher than 99%, besides the DCU. The ester was then suspended in THF (100 mL), cooled to 0 ° C., and 1 N LiOH (61 mL) was added. After stirring for 15 minutes, the mixture was filtered and the filtrate was washed with methylene chloride (2×150 mL). The alkaline solution then was cooled to 0° C. and the pH was adjusted to 2.0 with 1 N HCl. The title compound was isolated by filtration and was washed once with water, leaving 11.3 g of a white powder after drying. The material was suspended in methylene chloride (300 mL) and petroleum ether (300 mL) was added. Filtration and wash afforded 7.1 g (69%) after drying.

HPLC showed a purity of 99% $R_7$=19.5 minutes, and a minor impurity at 12.6 minutes (approx. 1%) most likely the Z-deprotected monomer. Anal. for $C_{23}H_{29}N_5O_8$ found(calc.) C, 54.16(54.87); H; 5.76(5.81) and N, 13.65(13.91). $^1$H-NMR (250 MHZ, DMSO-$d_6$). 10.78 (bs, 1H, $CO_2\underline{H}$; 7.88 (2 overlapping doublets, 1H, Cyt H-5); 7.41–7.32 (m, 5H, Ph); 7.01 (2 overlapping doublets, 1H, Cyt H-6); 6.94 & 6.78 (unresolved triplets, 1H, BOC—N$\underline{H}$); 5.19 (s, 2H, PhC $\underline{H}_2$); 4.81 & 4.62 (s, 2H, $CH_2CON$); 4.17 & 3.98 (s, 2H, C $\underline{H}_2CO_2H$); 3.42–3.03 (m, includes water, $CH_2CH_2$) and 1.38 & 1.37 (s, 9H, '-Bu). $^{13}$C-NMR. 150.88; $\overline{128.52}$; 128.18; 127.96; 93.90; 66.53; 49.58 and 28.22. IR: Frequency in $cm^{-1}$. 3423, 3035, 2978, 1736, 1658, 1563, 1501 and 1456.

EXAMPLE 7

Synthesis of 9-carboxymethyladenine Ethyl Ester

Adenine (10 g, 74 mmol) and potassium carbonate (10.29 g, 74 mmol) were suspended in DMF and ethyl bromoacetate (8.24 mL, 74 mmol) was added. The suspension was stirred for 2.5 h under nitrogen at room temperature and then filtered. The solid residue was washed three times with DMF (10 mL). The combined filtrate was evaporated to dryness, in vacuo. Water (200 mL) was added to the yellowish-orange solid material and the pH adjusted to 6 with 4 N HCl. After.stirring at 0° C. for 10 minutes, the solid was filtered off, washed with water, and recrystallized from 96% ethanol (150 mL). The title compound was isolated by filtration and washed thoroughly with ether. Yield: 3.4 g (20%). M.p. 215.5–220° C. Anal. for $C_9H_{11}N_5O_2$found(calc.): C, 48.86 (48.65); H; 5.01(4.91); N, 31.66(31.42). 1H-NMR (250 MHZ; DMSO-$d_6$): 7.25 (bs, 2H, $NH_2$), 5.06 (s, 2H, $NCH_2$), 4.17 (q, 2H, J=7.11 Hz, $OCH_2$) and 1.21 (t, 3H, J=7.13 Hz, $NCH_2$). $^{13}$C-NMR. 152.70, 141.30, 61.41, 43.97 and 14.07. FAB-MS. 222 (MH+). IR: Frequency in $cm^{-1}$. 3855, 3274, 3246, 3117, 2989, 2940, 2876, 2753, 2346, 2106, 1899, 1762, 1742, 1742, 1671, 1644, 1606, 1582, 1522, 1477, 1445 and 1422. The position of alkylation was verified by X-ray crystallography on crystals, which were obtained by recrystallization from 96% ethanol.

Alternatively, 9-carboxymethyladenine ethyl ester can be prepared by the following procedure. To a suspension of adenine (50 g, 0.37 mol) in DMF (1100 mL) in 2 L three-necked flask equipped with a nitrogen inlet, a mechanical stirrer and a dropping funnel, was added 16.4 g (0.407 mol) of hexane-washed sodium hydride-mineral oil dispersion. The mixture was stirred vigorously for 2 hours, after which ethyl bromoacetate (75 mL, 0.67 mol) was added dropwise over the course of 3 hours. The mixture was stirred for one additional hour, after which tlc indicated complete conversion of adenine. The mixture was evaporated to dryness at 1 mm Hg and water (500 mL) was added to the oily residue which caused crystallization of the title compound. The solid was recrystallised from 96% ethanol (600 mL). Yield (after drying): 53.7 g (65.6%). HPLC (215 mm) purity>99.5%.

EXAMPLE 8

Synthesis of N'benzyloxyearbonyl-9-carboxymethyladenine Ethyl Ester

9-Carboxymethyladenine ethyl ester (3.4 g, 15.4 mmol) was dissolved in dry DMF (50 mL) by gentle heating, cooled to 20° C., and added to a solution of N-ethyl-benzyloxycarbonylimidazole tetrafluoroborate (62 mmol) in methylene chloride (50 mL) over a period of 15 minutes in an ice bathe Some precipitation was observed. The ice bath was removed and the solution was stirred overnight. The reaction mixture was treated with saturated sodium hydrogen carbonate (100 mL). After stirring for 10 minutes, the phases were separated and the organic phase was washed successively with one volume of water, dilute potassium hydrogen sulfate (twice), and with saturated sodium chloride The solution was dried over magnesium sulfate and evaporated to dryness, in vacuo, which afforded 11 g of an oily material. The material was dissolved in methylene chloride (25 mL), cooled to 0° C., and precipitated with petroleum ether (50 mL). This procedure was repeated once to give 3.45 g (63%) of the title compound. M.p. 132–35° C. Analysis for $C_{17}H_{17}N_5O_4$ found (calc.): C, 56.95(57.46); H; 4.71(4.82); N, 19.35(19.71). $^1$H-NMR (250 MHZ; $CDCl_3$): 8.77 (s, 1H, H-2 or H-8); 7.99 (s, 1H, H-2 or H-8); 7.45–7.26 (m, 5H, Ph); 5.31 (s, 2H, N—$CH_2$); 4.96 (s, 2H, Ph—$CH_2$); 4.27 (q, 2H, J=7.15 Hz, $CH_2C\overline{H}_3$) and 1.30 (t, 3H, J=$\overline{7.15}$ Hz, $CH_2CH_3$). $^{13}$C-NMR: $\overline{153.09}$; 143.11; 128.66; 67.84; 62.51; $44.\overline{24}$ and 14.09. FAB-MS: 356 (MH+) and 312 (MH+—$CO_2$). IR: frequency in $cm^{-1}$: 3423; 3182; 3115; 3031; 2981; 1747; 1617; 15.87; 1552; 1511; 1492; 1465 and 1413.

EXAMPLE 9

Synthesis of $N^6$benzyloxyearbonyl-9-carboxymethyladenine $N^6$-Benzyloxycarbonyl-9-carboxymethyladenine ethyl ester (3.2 g, 9.01 mmol) was mixed with methanol (50 mL) cooled to 0° C. Sodium hydroxide solution (2 N, 50 mL) was added, whereby the material quickly dissolved. After 30 minutes at 0° C., the alkaline solution was washed with methylene chloride (2×50 mL). The pH of the aqueous solution was adjusted to 1 with 4 N HCl at 0° C., whereby the title compound precipitated. The yield after filtration, washing with water, and drying was 3.08 g (104%). The product contained salt, and the elemental analysis reflected that Anal. for $C_{15}H_{13}N_5O_4$ found(calc.): C: 46.32(55.05); H; 4.24(4.00); N, 18.10(21.40) and C/N: 2.57(2.56). $^1$H-NMR (250 MHZ; DMSO-$d_6$): 8.70 (s, 2H, H-2 and H-8); 7.50–7.35 (m, 5, Ph); 5.27 (s, 21, N—$CH_2$); and 5.15 (s, 2H, Ph—$CH_2$). $^{13}$C-NMR. 168.77, $152.\overline{54}$ 151.36, 148.75, 145.13, 128.51, 128.17,127.98, 66.76 and 44.67.IR (KBr) 3484; 3109; 3037; 2966; 2927; 2383; 1960; 1739; 1688; 1655; 1594; 1560; 1530; 1499; 1475; 1455; 1429 and 1411. FAB-MS: 328 (MH+) and 284 (MH+—$CO_2$). HPLC (215 nm, 260 m) in system 1: 15.18 min, minor impurities all less than 2%.

EXAMPLE 10

Synthesis of $N^6$-benzyloxyearbonyl-1-(BOC-aeg) adenine Ethyl Ester

N'-BOC-aminoethylglycine ethyl ester (2 g, 8.12 mmol), DhbtOH (1.46 g, 8.93 mmol) and N6-benzyloxycarbonyl-9-carboxymethyl adenine (2.92 g, 8.93 mmol) were dissolved in DMF (15 mL). Methylene chloride (15 mL) was then added. The solution was cooled to 0° C. in in ethanol/ice bath. DCC (2.01 g, 9.74 mmol) was added. The ice bath was removed after 2.5 h and stirring was continued for another 1.5 hour at ambient temperature. The precipitated DCU was removed by filtration and washed once with DMF (15 mL), and twice with methylene chloride (2×15 mL). To the combined filtrate was added more methylene chloride (100 mL). The solution was washed successively with dilute sodium hydrogen carbonate (2×100 mL), dilute potassium hydrogen sulfate (2×100 mL), and saturated sodium chloride (1×100 mL). The organic phase was evaporated to dryness, in vacuo, which afforded 3.28 g (73%) of a yellowish oily substance. HPLC of the raw product showed a purity of only 66% with several impurities, both more and less polar than the main peak. The oil was dissolved in absolute ethanol (50 mL) and activated carbon was added. After stirring for 5 minutes, the solution was filtered. The filtrate was mixed with water (30 mL) and was allowed to stir overnight. The next day, the white precipitate was removed by filtration, washed with water, and dried, affording 1.16 g (26%) of a material with a purity higher than 98% by HPLC. Addition of water to the mother liquor afforded another 0.53 g of the product with a purity of approx. 95%. Anal. for $C_{26}H_{33}N_7O_7 \cdot H_2O$ found(calc.) C, 55.01(54.44; H; 6.85 (6.15) and N, 16.47(17.09). $^1$H-NMR (250 MHZ, CDCl$_3$) 8.74 (s, 1H, Ade H-2); 8.18 (b. s, 1H, ZNH); 8.10 & 8.04 (s, 1H, H-8); 7.46–7.34 (m, 5H, Ph); 5.63 (unres. t, 1H, BOC—NH); 5.30 (s, 2H, PhCH$_2$); 5.16 & 5.00 (s, 2H, C H$_2$CON); 4.29 & 4.06 (s, 2H, CH$_2$CO$_2$H); 4.20 (q, 2H, OC H$_2$CH$_3$); 3.67–3.29 (m, 4H, CH$_2$CH$_2$CH$_2$); 1.42 (s, 9H, t-Bu) and 1.27 (t, 3H, OCH$_2$CH$_3$). The spectrum shows traces of ethanol and DCU.

EXAMPLE 11

Synthesis of N$^6$-benzyloxycarbonyl-1-(BOC-aeg) adenine

N$^6$-Benzyloxycarbonyl-1-(BOC-aeg)adenine ethyl ester (1.48 g, 2.66 mmol) was suspended in THF (13 mL) and the mixture was cooled to 0° C. Lithium hydroxide (8 mL, 1 N) was added. After 15 minutes of stirring, the reaction mixture was filtered, extra water (25 mL) was added, and the solution was washed with methylene chloride (2×25 mL). The pH of the aqueous solution was adjusted to 2 with 1 N HCl. The precipitate was isolated by filtration, washed with water, and dried, affording 0.82 g (58%) of the product. The product was additionally precipitated twice from methylene chloride/petroleum ether. Yield (after drying): 0.77 g (55%). M.p. 119° C. (decomp.). Anal. for $C_{24}H_{29}N_7O \cdot H_2O$ found (calc.) C, 53.32(52.84); H; 5.71(5.73); N, 17.68(17.97). FAB-MS. 528.5 (MH+). $^1$H-NMR (250 MHZ, DMSO-d$_6$). 12.75 (very b, 1H, CO$_2$H); 10.65 (bs, 1H, ZNH); 8.59 (d, 1H, J=2.14 Hz, Ade H-2); 8.31(s, 1H, Ade H-8); 7.49–7.31 (m, 5H, Ph); 7.03 & 6.75 (uresol. t, 1H, BOC—NH); 5.33 & 5.16 (s, 2H, CH$_2$CON); 5.22 (s, 2H, PhCH$_2$); 4.34–3.99 (s, 2H, CH$_2$CO$_2$H); 3.54–3.03 (multiplets, includes water, C H$_2$CH$_2$) and 1.39 & 1.37 (s, 9H, t-Bu). $^{13}$C-NMR. 170.4; 166.6; 152.3; 151.5; 149.5; 145.2; 128.5; 128.0; 127.9; 66.32; 47.63; 47.03; 43.87 and 28.24.

EXAMPLE 12

Synthesis of 2-amino-6-chloro-9-carboxymethylpurine

To a suspension of 2-amino-6chloropurine (5.02 g, 29.6 mmol) and potassium carbonate (12.91 g, 93.5 mmol) in DMF (50 mL) was added bromoacetic acid (4.7 g, 22.8 mmol). The mixture was stirred vigorously for 20 h under nitrogen. Water (150 mL) was added and the solution was filtered through celite to give a clear yellow solution. The solution was acidified to a pH of 3 with 4 N hydrochloric acid. The precipitate was filtered and dried, in vacuo, over sicapent Yield: 3.02 g (44.8%). $^1$H-NMR(DMSO-d$_6$) δ: 4.88 ppm (s, 2H); 6.95 (s, 2H); 8.10 (s, 1H).

EXAMPLE 13

Synthesis of 2-amino-6-benzyloxy-9-carboxymethylpurine

Sodium (2 g 87 mmol) was dissolved in benzyl alcohol (20 mL) and heated to 130° C. for 2 h. After cooling to 0° C, a solution of 2-amino-6-chloro-9-carboxymethylpurine (4.05 g, 18 mmol) in DMF (85 mL) was slowly added, and the resulting suspension stirred overnight at 20° C. Sodium hydroxide solution (1 N, 100 mL) was added and the clear solution was washed with ethyl acetate (3×100 mL). The water phase was then acidified to a pH of 3 with 4 N hydrochloric acid. The precipitate was taken up in ethyl acetate (200 mL), and the water phase was extracted with ethyl acetate(2×100 mL). The combined organic phases were washed with saturated sodium chloride solution (2×75 mL), dried with anhydrous sodium sulfate, and evaporated to dryness, in vacua. The residue was recrystallized from ethanol (300 mL). Yield, after drying in vacuo, over sicapent: 2.76 g (52%). M.p. 159–65° C. Anal. (calc.; found): C. (56.18; 55.97); H, (4.38;.4.32); N, (23.4; 23.10). $^1$H-NMR (DMSO-d$_6$) δ: 4.82 (s, 2H); 5.51 (s, 2H); 6.45 (s, 2H); 7.45 (m, 5H);7.82 (s, 1H).

EXAMPLE 14

Synthesis of N-([2-amino-6-benzyloxy-purine-9-yl]-acetyl)-N-(2-BOC-aminoethyl)glycine [BOC-Gaeg-OH monomer]

2-Amino-6-benzyloxy-9-carboxymethyl-purine (0.5 g, 1.67 mmol), methyl-N(2-[tert-butoxycarbonylamino]ethyl) glycinate (0.65 g, 2.8 mmol), diisopropylethyl amine (0.54 g, 4.19 mmol), and bromo-tris-pyrrolidino-phosphonium-hexafluoro-phosphate (PyBroP®) (0.798 g, 1.71 mmol) were stirred in DMF (2 mL) for 4 h. The clear solution was poured into an ice-cooled solution of sodium hydrogen carbonate (1 N, 40 mL) and extracted with ethyl acetate (3×40 mL,). The organic layer was washed with potassium hydrogen sulfate solution (1 N, 2×40 mL), sodium hydrogen carbonate (1N, 1×40 mL) and saturated sodium chloride solution (60 mL). After drying with anhydrous sodium sulfate and evaporation in vacuo, the solid residue was recrystallized from 2:1 ethyl acetate/hexane (20 mL) to give the methyl ester in 63% yield. (MS-FAB 514 (M+1). Hydrolysis was accomplished by dissolving the ester in 1:2 ethanol/water (30 mL) containing concentrated sodium hydroxide (1 mL). After stirring for 2 h, the solution was filtered and acidified to a pH of 3, by the addition of 4 N hydrochloric acid. The title compound was obtained by filtration. Yield: 370 mg (72% for the hydrolysis). Purity by HPLC was more than 99%. Due to the limited rotation around the secondary amide several of the signals were doubled in the ratio 2:1 (indicated in the list by mj for major and mi for minor). $^1$H-NMR(250, MHZ, DMSO-d$_6$) δ: 1.4 (s, 9H); 3.2 (m, 2H); 3.6 (m, 2H); 4.1 (s, mj, CONRC H$_2$COOH); 4.4 (s, mi, CONRCH$_2$COOH); 5.0 (s, mi, Gua-C H$_2$CO—); 5.2 (s, mj, Gua-CH$_2$CO); 5.6 (s, 2H); 6.5 s, 2H); 6.9 (m, mi, BOC—NH); 7.1 (m, mj, BOC—NH); 7.5 (m, 3H); 7.8 (s, 1H); 12,8 (s, 1H). $^{13}$C-NMR 170.95; 170.52; 167.29; 166.85; 160.03; 159.78; 155.84; 154.87; 140.63; 136.76; 128.49; 128.10; 113.04; 78.19; 77.86; 66.95; 49.22; 47.70; 46.94; 45.96; 43.62; 43.31 and 28.25.

EXAMPLE 15

Synthesis of ethyl-N$^6$-(benzyloxycarbonyl)-2,6-diaminopurin-9-yl-acetate

To a suspension of 2,6diaminopurine (3 g, 19.46 mmol) in dry DMF (90 mL) was added NaH (60% in oil, 0.87 g, 21.75 mmol). After 1 hour ethyl bromoacetate (4.23 g, 25.34 mmol) was added. The reaction mixture became homogenous in 30 minutes and was allowed to stir for an additional 90 minutes. The DMF was removed in vacuo resulting in a tan powder. The tan powder was then refluxed with 1,4-dioxane (200 mL) for 10 minutes and filtered through celite. The solution was concentrated to give a light yellow powder. To the light yellow powder (5.52 g) in 1,4-dioxane (150 mL) was added freshly prepared N-benzyloxycarbonyl-N'-methylimidazolium triflate (10.7 g, 29.2 mmol). The reaction mixture was stirred at room temperature for 16 h resulting in a reddish solution. The dioxane was removed in vacuo and the crude material was recrystallized from MeOH:diethyl ether to give 4.56 g (63%) of the title compound as a cream-colored solid.

$^1$H NMR (DMSO-$d_6$) δ: 10.12 (bs, 1H), 7.43 (m, 5H), 6.40 (bs, 2H), 5.17 (s, 2H), 4.94 (s, 2H), 4.18 (q, J=7.2, 3H), 1.21 (t, J=7.2, 3H). $^{13}$C NMR (DMSO-$d_6$) ppm: 167.81, 159.85, 154.09, 152.07, 149.77, 140.62, 136.42, 128.22, 127.74, 127.61, 166.71.65.87, 61.21, 43.51, 13.91.

EXAMPLE 16

Synthesis of $N^6$-(benzyloxycarbonyl)-2,6-diaminopurin-9-yl-acetic acid

Ethyl-$N^6$-(benzyloxycarbonyl)-2,6-diaminopurin-9-yl-acetate (3 g, 8.1 mmol) was dissolved in NaOH (2 N, 30 mL). After 1 h the solution was acidified to pH 2.5 with 2 M HCl. The precipitate was filtered, washed with water, and dried to give 2.82 g (98%) of the title compound as a white solid.

IR (KBr): 3300, 3095, 1750, 1630, 1590, 1410. $^1$H NMR (DMSO-$d_6$) δ: 10.11 (s, 1H), 7.91 (s, 1H),7.45–7.33 (m, 5H), 6.40 (s, 2H), 5.17 (s, 2H), 4.83 (s, 2H).

EXAMPLE 17

Synthesis of BOC-aminoacetaldehyde

The title compound was prepared according to a published literature procedure (Dueholm et al., *Organic Preparations and Procedures Intl.*, 1993, 25, 457).

EXAMPLE 18

Synthesis of ε-(2-chlorobenzyloxycarbonyl)-lysine allyl ester

The title compound was prepared according to a published literature procedure (Waldmann and Horst, *Liebigs Ann. Chem*, 1983, 1712).

EXAMPLE 19

Synthesis of N-(BOC-aminoethyl)ε-(2-chlorobenzyloxycarbonyl)-lysine allyl ester

ε-(2-chlorobenzyloxycarbonyl)-lysine allyl ester (from example 18) was dissolved in methanol (50 mL) and cooled to 0° C. To the resulting solution was added sodium cyanoborohydride (5.9 mmol) followed by acetic acid (0.75 mL). After 5 minutes BOC-amino-acetaldehyde (13.3 mmol) was added and the reaction mixture was stirred for an additional 1 h. The methanol was removed in vacuo and the oil was dissolved in ethyl acetate (40 mL), washed with saturated aqueous NaHCO$_3$, brine, dried over Na$_2$SO$_4$ and concentrated to give a clear colorless oil. This oil was dissolved in dry ether (80 mL), cooled to −20° C., and a molar equivalent of HCl in ether was added slowly. The resulting white solid was collected by filtration and air dried Precipitation of tie air-dried white solid from dry ember gave analytically pure title compound.

EXAMPLE 20

Synthesis of N-(BOC-aminoethyl)-N-[$N^6$-(benzyloxycarbonyl)-2,6-diaminopurin -9y-acetyl]-ε (2-chlorobenzyloxycaronyl)-lysine allyl ester To $N^6$-(benylaxycarbonyl)-2,6-diaminopurin-9-yl-acetic acid (3–6 g, 10.5 mmol) in DMF (150 mL) was added N,N-diisopropylethylamine (275 mL, 21 mmole), and N-(BOC-aminoethyl -ε-(2-chlorobenyoxycaronyl)-lysine allyl ester hydrochloride (7.31 gm, 15.8 mmol). The reaction mixture was stirred under nitrogen for 20 minutes and bromo-tris- pyrrolidino-phosphonium hexafluorophosphate (PyBrop, 5.4 gm, 11.6 mmol) was added. The reaction mixture was stirred overnight at room temperature under an atmosphere of nitrogen gas. The resulting mixture was concentrated and dissolved in ethyl acetate. The ethyl acetate solution was washed with aqueous saturated sodium bicarbonate, separated and concentrated. The crude material was purified by silica gel flash column chromatography using ethyl acetate:hexane:methanol (6:3:1, v/v/v), as the eluent. Concentration and drying of the appropriate fractions gave 3.1 g (37%) of the title compound.

EXAMPLE 21

Synthesis of N-(BOC-aminoethyl)-N-[$N^6$-(benzyloxycarbonyl)-2,6-diaminopurin-9-yl-acetyl]-ε-(2-chlorobenzyloxycarbonyl)-lysine To N-(BOC-aminoethyl)-N-[$N^6$(benzyloxycarbonyl)-2,6-diaminopurin-9-yl-acetyl]-ε-(2-chlorobenzyloxycarbonyl)-lysine allyl ester hydrochloride (3.1 gm, 3.93 mmol) was added THF (100 mL) morpholine (3.5 mL, 39.3 mmol), and tetrakis(trisphenylphosphine)-palladium(0) (0.45 gm, 0.393 mmol). The reaction mixture was stirred under an atmosphere of nitrogen for 2.5 h at room temperature. The resulting mixture was concentrated and dissolved in ethyl acetate. The ethyl acetate solution was washed with aqueous satuated potassium hydrogen sulfate (that was half-diluted with water), separated and concentrated. The crude material was purified by silica gel flash column chromatography using chloroform:methanol (9:1, v/v), as the eluent. Concentration and drying of the appropriate fractions gave 1.25 g (42%) of the title compound.

EXAMPLE 22

Preparation of Guanine Monomer (BOC-Gaek-OH)

To $N^6$-benzyl-9-carboxymethylene-guanine (2.63 g, 8.78 mmol) was added DIEA (2.6 mL, 20 mmol), DMF (30 mL), dichloromethane (70 mL), and N-(BOC-aminoethyl)-ε-(2-chlorobenzyloxycarbonyl)-lysine allyl ester (3.7 g, 8.04 mmol). The reaction mixture was stirred under nitrogen for 20 minutes. PyBrop (4 g, 8.58 mmol) was added and the reaction mixture stirred for an additional 16 h. The reaction mixture was concentrated and the residue was purified by silica gel flash column chromatography using chloroform/hexanes/methanol (12:7:1, v/v/v) to give 4 g (60%) of the title compound as the allyl ester.

To the allyl ester (4 g, 5.37 mmol) was added THF (100 mL), tetrakispalladium(0) (0.18 g, 0.15 mmol), and morpholine (6.1 mL, 70 mmol). The reaction mixture was stirred under nitrogen for 2.5 h and concentrated. The residue was purified by silica gel flash column chromatography using chloroform/hexanes/methanol (11:8:1, v/v/v) to give 2.67 g (60%) of the title compound.

EXAMPLE 23

Preparation of Adenine Monomer (BOC-Aaek-OH)

The procedure used for the guanine monomer in Example 22 above was followed for the synthesis of the adenine monomer using N6-benzyl-9-carboxymethylene-adenine.

EXAMPLE 24

Preparation of Cytosine Monomer (BOC-Caek-OH)

To N-(BOC-aminoethyl)-ε-(2-chlorobenzyloxycarbonyl)-lysine allyl ester (8.21 g, 17.7 mmol), were added triethylamine (10 mL, 98 mmol) and dichloromethane (200 mL). The solution was cooled to about 0° C. in an ice bath under nitrogen. To the cooled solution was added chloroacetyl chloride (2.2 mL, 27.6 mmol) over 10 minutes and the reaction mixture stirred at room temperature for 16 h. The reaction mixture was concentrated and the residue was purified by silica gel flash column chromatography using ethyl acetate/hexanes (1:1, v/v) to give 6.54 g (68%) of the N-acetylated lysine backbone.

Cytosine was protected at the $N^4$- position by treatment with benzyl chloroformate in pyridine at 0° C. to give $N^4$-benzyl-cytosine.

To N4-benzyl-cytosine (1.31 g, 5.34 mmol) was added DMF (200 mL), and 60% NaH in mineral oil (0.22 g, 5.4 mmol) and the resulting mixture was stirred under nitrogen for 30 minutes. To the resulting mixture was added the N-acetylated lysine backbone (2.9 g, 5.34 mmol) in DMF (25 mL) and the mixture stirred for 16 h. The reaction mixture was concentrated and the residue dissolved in dichloromethane (250 mL). The dichloromethane phase was washed with water (200 mL) and concentrated. The resulting residue was purified by silica gel flash column chromatography using dichloromethane:hexanes: methanol (8:2:1) to give 2.4 g (85%) of the cytosine attached to the aminoethyl-lysine backbone as the allyl ester.

The allyl ester is converted to the active monomer by deprotection using palladium following the procedure used in Example 22 above to give 1.05 g (46%) of the title compound.

EXAMPLE 25

Preparation of Thymine Monomer (BOC-Taek-OH)

The thymine monomer was prepared following the procedure of Example 24 above.

EXAMPLE 26

Solid Phase Synthesis of H-Taeg-Aaeg-[-Taeg]$_8$-Lys-NH$_2$(SEQ ID NO: 4)

(a) Stepwise Assembly of BOC-Taeg-A(Z)aeg-[Taeg]-Lys(ClZ)-MBHA Resin

About 0.3 g of wet BOC-[Taeg]-Lys(ClZ)-MBHA resin was placed in a 3 mL SPPS reaction vessel. BOC-Taeg-A(Z)aeg-[Taeg]$_8$-Lys(ClZ)-MBHA resin (SEQ ID NO: 4) was assembled by in situ DCC coupling (single) of the A(Z)aeg residue utilizing 0.19 M of BOC-A(Z)aeg-OH together with 0.15 M DCC in 2.5 mL of 50% DMF/CH$_2$Cl$_2$ and a single coupling with 0.15 M BOC-Taeg-OPfp in neat CH$_2$Cl$_2$ ("Synthetic Protocol I"). The synthesis was monitored by the quantitative ninhydrin reaction, which showed about 50% incorporation of A(Z)aeg and about 96% incorporation of Taeg.

(b) Cleavage, Purification, and Identification of H-Taeg-Aaeg-[Taeg]$_8$-Lys-NH$_2$(SEQ ID NO: 4)

The protected BOC-Taeg-A(Z)aeg-[Taeg]$_8$-Lys(ClZ)-BHA resin (SEQ ID NO: 4) was treated with 50% trifluoroacetic acid in methylene chloride to remove the N-terminal BOC group (which is a precursor of the potentially harmful tert-butyl cation) prior to the HF cleavage. Following neutralization and washing performed in a way similar to those of steps 2–4 in "Synthetic Protocol 1"), and drying for 2 h in vacuum, the resulting 53.1 mg of H-[Taeg]$_5$-BHA resin was cleaved with 5 mL of HF:anisole (9:1, v/v) while stirring at 0° C. for 60 minutes. After removal of HF, the residue was stirred with dry diethyl ether (4×15 mL, 15 minutes each) to remove anisole, filtered under gravity through a fritted glass funnel, and dried. The PNA was then extracted into a 60 mL (4×15 mL, stirring 15 minutes each) 10% aqueous acetic acid solution. Aliquots of this solution were analyzed by analytical reverse-phase HPLC to establish the purity of the crude PNA. The main peak at 13 minutes accounted for about 93% of the total absorbance. The remaining solution was frozen and lyophilized to afford about 15.6 mg of crude material. The main peak at 14.4 minutes accounted for less than 50% of the total absorbance. A 0.5 mg portion of the crude product was purified to give approximately 0.1 mg of H-Taeg-Aaeg-[Taeg]$_8$-Lys-NH$_2$. For (MH+)$^+$ the calculated m/z value was 2816.16 and the measured m/z value was 2816.28.

(c) Synthetic Protocol I (1) BOC-deprotection with TFA/CH$_2$Cl$_2$ (1:1, v/v), 2.5 mL, 3×1 minute and 1×30 minutes; (2) washing with CH$_2$Cl$_2$, 2.5 mL, 6×1 minute; (3) neutralization with DIEA/CH$_2$Cl$_2$ (1:19, v/v), 2.5 mL, 3×2 minutes; (4) washing with CH$_2$Cl$_2$, 2.5 mL, 6×minute, and drain for 1 minute; (5) 2–5 mg sample of PNA-resin was removed and dried thoroughly for a quantitative ninhydrin analysis to determine the substitution; (6) addition of 0.47 mmol (0.25 g) BOC—A(Z)aeg-OH dissolved in 1.25 mL of DMF followed by addition of 0.47 mmol (0.1 g) DCC in 1.25 mL of CH$_2$Cl$_2$ or 0.36 mmol (0.2 g) BOC-Taeg-OPfp in 2.5 mL of CH$_2$Cl$_2$; the coupling reaction was allowed to proceed for a total of 20–24 h while shaking; (7) washing with DMF, 2.5mL, 1×2 minutes; (8) washing with CH$_2$Cl$_2$, 2.5mL, 4×minute; (9) neutralization with DIEA/CH$_2$Cl$_2$ (1:19, v/v), 2.5 mL, 2×2 minutes; (10) washing with CH$_2$Cl$_2$, 2.5 mL, 6×1 minute; (11) 2–5 mg sample of protected PNA-resin was removed and dried thoroughly for a quantitative ninhydrin analysis to determine the extent of coupling; (12) blocking of unreacted amino groups by acetylation with a 25 mL mixture of acetic anhydride/pyridine/CH$_2$Cl$_2$ (1:1:2, v/v/v) for 2 h (except after the last cycle); and (13) washing with CH$_2$Cl$_2$, 2.5 mL, 6×1 minute; (14) 2×2–5 mg samples of protected PNA-resin are removed, neutralized with DIEA/CH$_2$Cl$_2$ (1:19, v/v) and washed with CH$_2$Cl$_2$ for ninhydrin analyses.

EXAMPLE 27

Solid Phase Synthesis of H-[Taeg]$_2$-Aaeg-[Taeg]$_5$-Lys-NH$_2$ (a) Stepwise Assembly of BOC-[Taeg]$_2$-A(Z)aeg-[Taeg]$_5$-Lys(ClZ)-MBHA Resin About 0.5 g of wet BOC-[Taeg]$_5$-Lys(ClZ)-MBHA resin was placed in a 5 mL SPPS reaction vessel. BOC-[Taeg]$_2$-A(Z)aeg-[Taeg]$_5$-Lys(ClZ)MBHA resin was assembled by in situ DCC coupling of both the A(Z)aeg and the Taeg residues utilising 0.15 M to 0.2 M of protected PNA monomer (free acid) together with an equivalent amount of DCC in 2 mL neat CH$_2$Cl$_2$ ("Synthetic Protocol II"). The synthesis was monitored by the quantitative ninhydrin reaction which showed a total of about 82% incorporation of A(Z)aeg after coupling three times (the first coupling gave about 50% incorporation; a fourth HOBt-mediated coupling in 50% DMF/CH$_2$Cl$_2$ did not increase the total coupling yield significantly) and quantitative incorporation (single couplings) of the Taeg residues.

(b) Cleavage, Purification, and Identification of H-[Taeg]$_2$-Aaeg-[Taeg]$_5$-Lys-NH$_2$ The protected BOC-[Taeg]$_2$-A(Z)aeg-[Taeg]$_5$-Lys(ClZ)-BHA resin was treated as described in Example 26(b) to yield about 16.2 mg of crude material upon HF cleavage of 102.5 mg dry H-[Taeg]$_2$-A(Z)aeg-[Taeg]$_5$-Lys(ClZ)BHA resin. A small portion of the crude product was purified. For (MH+)$^+$, the calculated m/z value was 2050.85 and the measured m/z value was 2050.90.

(c) Synthetic Protocol II (1) BOC-deprotection with TFA/CH$_2$Cl$_2$ (1:1, v/v), 2 mL, 3×1 minute and 1×30 minutes; (2) washing with CH$_2$Cl$_2$, 2 mL, 6×1 minute; (3) neutralization with DIEA/CH$_2$Cl$_2$ (1:19, v/v), 2 mL, 3×2 minutes; (4) washing with CH$_2$Cl$_2$, 2 mL, 6×1 minute, and drain for 1 minute; (5) 2–5 mg sample of PNA-resin was removed and dried thoroughly for a quantitative ninhydrin analysis to determine the substitution; (6) addition of 0.44 mmol (0.23 g) BOC-A(Z)aeg-OH dissolved in 1.5 mL of CH$_2$Cl$_2$ followed by addition of 0.44 mmol (0.09 g) DCC in 0.5 mL of CH$_2$Cl$_2$ or 0.33 mmol (0.13 g) BOC-Taeg-OH in 1.5 mL of CH$_2$Cl$_2$ followed by addition of 0.33 mmol (0.07 g) DCC in 0.5 mL of CH$_2$Cl$_2$; the coupling reaction was allowed to proceed for a total of 20–24 h with shaking; (7) washing with DWF, 2 mL, 1×2 minutes; (8) washing with CH$_2$Cl$_2$, 2 mL, 4×1 minute; (9) neutralization wit DIEA/CH$_2$CH$_2$ (1:19, v/v), 2 mL, 2×2 minutes; (10) washing with CH$_2$Cl$_2$, 2 mL, 6×1 minute; (11) 2–5 mg sample of protected PNA-resin was removed and dried thoroughly for a quantitative ninydrin analysis to the extent of coupling; (12) blocking of unreacted amino groups by acerylation with a 25 mL mixture of acetic anhydride/pyridine/CH$_2$Cl$_2$ (1:1:2, v/v/v) for 2 h (except after the last cycle); (13) washing with CH$_2$Cl$_2$, 2 mL, 6×1 minute; and (14) 2×2–5 mg samples of protected PNA-resin were removed, neutralized with DIEA/CH$_2$Cl$_2$ (1:19, v/v) and washed with CH$_2$Cl$_2$ for ninhydrin analyses.

EXAMPLE 28

Standard Protocol for PNA Synthesis and Characterization

Instrument: Perceptive Biosystems 8909 Expedite.
Synthesis Scale: 2 μmole.
Reagents:
Wash A: 20% DMSO in NMP
Wash B: 2 M Collidine in 20% DMSO in NMP
Deblock: 50/a m-Cresol, 95% TFA
Neutralizer: 1 M DIEA in 20% DMSC in NMP
Cap: 0.5 M Acetic Anhydride, 1.5 M Collidine in 20% DMSO in NMP
Activator: 0.2 M HATU in DMF
Monomers: 0.22 M in 2 M Collidine (50% Pyridine in DMF)
Synthesis: The solid support (BOC-BHA-PEG-resin) is washed wit 708μl of Wash A. Deblock (177 μL) is passed trough the column 3 times over 6.3 minutes. The resin is then washed with 1416 μL of Wash A. The free amine is neutralized with 1063 μL of Neutralizer. The resin is washed with 1062 L of Wash B. Monomer and Activator (141 μL each) are slowly added to the column over 14 minutes. The resin is washed with a 708 μL of Wash B and 708 μL of Wash A. Unreacted and is capped with slow addition of 708 μL of Cap solution over 5 minutes. The resin is then washed 2124 μL of Wash A. The cycle is repeated until synthesis of the desired PNA sequence is completed.

Cleavage: The PNA-resin is washed with 5 mL of MeOH and dried under vacuum. The dried resin is emptied into a 1.5 mL Durapore ultrafree filter unit. Thioanisole (25 μL), 25 μL of m-Cresol, 100 μL of TFA and 100 μL of TFMSA is added to the resin, vortexed for about 30 seconds and allowed to stand for 2 h. The reaction mixture is then centrifuged for 5 minutes at 10 K and the inner tube with resin is removed. Approximately 1.5 mL of ether is added to the TFA solution to precipitate the product. The TFA solution is vortexed, followed by centrifugation at 10 K for 2 minutes. The ether is removed in vacuo. Ether precipitation and centrifugation are repeated an additional 2 times. The dry pellet is heated in a heat block (55° C.) for 15 to 30 minutes to remove excess ether and redissolved in 200 μL of H$_2$O. Solvent is added to 100 mg of Dowex Acetate Resin in a 1.5 mL Durapore ultrafree filter unit, vortexed, allowed to stand for 30 minutes and centrifuged at 10 K for 2 minutes.

Characterization: The absorbance of a 1 μL sample in 1 mL of H$_2$O is measured at 260 nm. Isopropanol (50%) in H$_2$O with 1% Acetic acid (100 μL) is added to 4 μL of the sample. This sample is characterized by electrospray mass spectrometry.

Common Abreviations
NMP: N-methyl pyrrolidinone
TFA: Trifluoroacetic acid
DIEA: N,N-Diisopropylethylamine
HATU: O-(7-azabenzotriazol-1-yl)-1,1,3,3-tetramethyluronium hexafluorophosphate
TFMSA: Trifluormethanesulfonic Acid

EXAMPLE 29

Synthesis and Cellular Uptake of Conjugated PNA Oligomers

Using the procedures of Example 28, the aminoethylglycine PNA monomers of examples 5 through 14, and monomers of Examples 15 through 21, the following PNA oligomers were synthesized.

| PNA | | Liposomes | Cellular Uptake |
|---|---|---|---|
| Fl-GGT-GCT-CAC-GCT-GGC-Lys-NH2 | (SEQ ID NO:5) | x | – |
| Fl-GGT-GCT-CAC-GCT-GGC-Lys-NH2 | (SEQ ID NO:5) | ✓ | – |
| Ada-Fl-GGT-GCT-CAC-TGC-GGC-Lys-NH2 | (SEQ ID NO:2) | x | – |
| Ada-Fl-GGT-GCT-CAC-TGC-GGC-Lys-NH2 | (SEQ ID NO:2) | ✓ | (+) |
| Fl-GGTk-GCTk-CAC-TkGC-GGC-Lys-NH2 | (SEQ ID NO:2) | x | – |
| Fl-GGTk-GCTk-CAC-TkGC-GGC-Lys-NH2 | (SEQ ID NO:2) | ✓ | – |

-continued

| PNA | Liposomes | Cellular Uptake |
|---|---|---|
| Ada-Fl-GGTh-GCTk-CAC-TkGC-GGC-Lys-NH2 (SEQ ID NO:2) | x | + |
| Ada-Fl-GGTk-GCTk-CAC-TkGC-GGG-Lys-NH2 (SEQ ID NO:2) | ✓ | + |

[(+) = PNA aggregates; − = no cellular uptake observed; + = cellular uptake observed; ✓ = presence of liposomes; x= absence of liposomes; Tk is thymine attached to an aminoethyl-lysine backbone; Lys is D-Lysine; Ada is adamantyl; and Fl is fluoresceinyl lysine.]

EXAMPLE 30

Synthesis of Linolenyl-TAG-CAG-AGG-AGC-TC (SEQ ID NO:1)

Linolenic acid (40 µmoles) was dissolved in coupling solvent (100 µL) (0.5 M DIEA in 20% DMSO/NMP), to which HATU (90 µL of 0.4 M) was added and the solution was mixed. After a 2 minute activation period, the solution was mixed with protected PNA resin (15.4 mg, 2 µmoles). After 1 hour, the resin was washed with 20% DMSO/NMP, $CH_2Cl_2$ and MeOH (about 3 mL each). The resulting linolenyl-conjugated PNA was cleaved from the solid support and characterized according to the procedure described in Example 28.

EXAMPLE 31

Synthesis of Oleyl-TAG-CAG-AGG-AGC-TC (SEQ ID NO:1)

Oleic acid (40 µmoles) was dissolved in coupling solvent (100 µL) (0.5 M DIEA in 20% DMSO/NMP), to which HATU (90 µL of 0.4 M) was added and the solution was mixed. After a 2 minute activation period, the solution was mixed with protected PNA resin (5.4 mg, 2 µmoles) After 1 hour, the resin was washed with 20% DMSO/NMP, $CH_2Cl_2$ and MeOH (about 3 mL each). The resulting linolenyl-conjugated PNA was cleaved from the solid support and characterized according to the procedure described in Example 28.

EXAMPLE 32

Synthesis of Caproyl-Gly-TAG-CAG-AGG-AGC-TC (SEQ ID NO:1)

Caproyl-gly (40 µmoles) was dissolved in coupling solvent (100 µL) (0.5 M DIEA in 20% DMSO/NMP), to which HATU (90 µL of 0.4 M) was added and the solution was mixed. After 2 minutes of activation The solution was mixed wit protected PNA resin (15.4 mg, 2 µmoles). After 1 hour, the resin was washed with 20% DMSO/NMP, $CH_2Cl_2$ and MeOH (about 3 mL each). The resulting PNA was cleaved from the solid support and characterized according to the procedure described in Example 28.

EXAMPLE 33

Synthesis of N-BOC-ε-(Fluoresceinyl carbonyl)-D-lysine and its ethyl ester

α-BOC protected lysine ethyl ester was treated with excess fluorescein isocyanate in a mixture of THF and DMF at room temperature for several hours. The reaction was monitored by tlc for the disappearance of the starting amino acid. The reaction was then treated with equal volumes of water and chloroform and the phases separated. The aqueous phase was extracted with more chloroform and the combined organic solutions so obtained, dried with magnesium sulfate. This solution was concentrated, in vacuo, and the crude product obtained was purified by column chromatography to afford the N-BOC-ε-(Fluoresceinyl carbonyl)-D-lysine ethyl ester.

The ethyl ester was hydrolyzed using 1M aqueous lithium hydroxide and tetrahydrofuran as solvent. The progress of the reaction was followed by tlc and upon completion the reaction mixture was treated wink water and then washed 2× with dichloromethane. The basic solution was then cooled to <10 C., neutralized with 1N HCl to a pH below 4 and the product extracted out using ethyl acetate. The organic extract was dried using magnesium sulfate, and concentrated in vacua to afford the N-BOC-ε-(Fluoresceinyl carbonyl)-D-lysine.

EXAMPLE 34

Coupling of N-BOC-e-(Fluoresceinyl carbonyl)-D-Lysine to PNA of sequence GGT-GCT-CAC-TGC-GGC-Lys-NH$_2$ (SEQ ID NO:2)

PNA of sequence GGT-GCT-CAC-TGC-GGC-Lys-NH$_2$ was synthesized following standard PNA synthesis protocols (as in examples 27 and 28) and commencing with lysine-derivatized synthesis resin. The N-terminal BOC group of the PNA bound to resin was deprotected using:

1. 3 mL of 1:1 v/v TFA/DCM 1×2 mins and then 1×0.5 hours
2. Washing with 3 mL DCM, 4×20 seconds. Washing with 3 mL DMF, 2×20 seconds Washing with 3 mL DCM, 2×20 seconds. Draining for 30 seconds.
3. Neutralizing with 3 mL DIEA/DCM, 1:19 v/v, 2×3 minutes.

Coupling of the Fluoresceinyl lysine was then performed according to the following steps:

1. Wash with DCM, 3 mL, 4×20 seconds. Drain for 1 minute.
2. Addition of 4 equivalents of DIC, and 4 equivalents of N-BOC-e-(Fluoresceinyl carbonyl)-D-Lysine dissolved in 1:1 v/v DCM(DMF (final concentration of the amino acid being (0.1M).
3. Coupling allowed to proceed for 0.5 hour with shaking at room temperature.
4. Drain for 20 seconds. Wash with 3 mL DMF, 2×20 seconds and 1×2 minutes. Wash with 3 mL DCM, 4×20 seconds.
5. Neutralize with 3 mL, DIEA/DCM, 1:19 v/v, 2×3 minutes. Wash with 3 mL DCM, 4×20 seconds; Drain for 1 minute.
6. Perform a qualitative Kaiser test. A negative result indicates near 100% coupling.

The BOC group was cleaved and then the PNA (Fl-GGT-GCT-CAC-TGC-GGC-Lys-NH$_2$) (SEQ ID NO:2) was cleaved and purified as in examples 27 and 28. Alternatively, the PNA is left attached to the resin and used for derivatization with a lipophilic group as in example 35.

EXAMPLE 35

Synthesis of Ada-Fl-GGT-GCT-CAC-TGC-GGC-Lys-NH$_2$ (SEQ ID NO:2)

The N-terminal BOC group of Fl-GGT-GCT-CAC-TGC-GGC-Lys-NH$_2$ (SEQ ID NO:2) PNA bound to the resin was first cleaved (as in example 34) and the free amino terminus then derivatized as follows:

100 μmole adamantoyl chloride was dissolved in 1:5 v/v DIEA/DMF was added to 2 μmole resin bound PNA (that is completely protected except at the N-terminus where the BOC group has been cleaved). After 1 hour of reaction, the resin was washed with 3 mL each of 20% NMP/DMSO, DCM and methanol. The PNA was cleaved from the resin and purified following standard protocols as in examples 27 and 28.

EXAMPLE 36

Synthesis of Adamantyl-Ahx-TAG-CAG-AGG-AGC-TC (SEQ ED NO:1)

Adamantyl carbonyl chloride (100 μmoles) was dissolved in DMF (1.0 mL) an d DIEA, (200 μmoles). Th is solution was mixed with protected PNA resin (15.4 mg, 2 μmoles) with an attached amino hexanoic acid group linking group. After 1 hour, the resin was washed with 20%, DMSO/NMP, CH$_2$Cl$_2$ and MeOH (about 3 mL each). The resulting PNA was cleaved from the solid support following known methods and techniques.

EXAMPLE 37

Preparation of PNA/Liposome

Liposomes containing the PNA Adanantyl-(Fl*)-TTT AGC AGC-LysNH$_2$(SEQ ID NO:3), where Fl* is a fluoresceinated PNA monomer, were prepared by a modification of the ethanol injection method described by Campbell. *Biotechniques,* 1995, 18, 1027. DOPE (dioleyl-L-a-phosphatidylethaolamine) (13.4 mmol) and DDAB (dimethyldiocadecylammonium bromide) (6.6 mmol) were dissolved in 1 L of 96% ethanol. A solution of PNA (10 mL, 2.5 mM) in DMSO wa s combined with the lipid mixture (40 mL). The resulting 50 mL of material was then rapidly added to sterile distilled H$_2$O (1 mL) while vortexing. The resulting PNA concentration in the liposome mix was 25 mM. For cell uptake experiments, the PNA-liposome mix (40 mL) was added to OptiMEM™ (1 mL) and fed to cells. The final concentration of PNA was 1 mM.

Liposome transfection reagents: Four commercially available transfection liposome reagents were employed: Lipofectin™ (Gibco BRL), Lipofectamine™ (Gibco BRL), Tfx-50™ (Promega) and DOTAP™ (Boehringer Mannheim). Each liposome reagent was mixed with conjugated PNA 1118 to give a final PNA concentration of 1 mM in the culture medium (1 mL). The optimal concentration of each liposome reagent in terms of PNA cell uptake was determined. The table below shows the amount of reagent used per mL of OptiMEM.

| Lipofectin ™ | Lipofectamine ™ | Tfx-50 ™ | DOTAP ™ |
|---|---|---|---|
| 2 mL | 4 mL | 10 mL | 10 mL |

Cells: The human carcinoma cell line HeLa was grown in RPMI 1640 medium containing Glutamax™, penicillin, streptomycin and fetal bovine serum. On the day preceding the experiment, the cells were plated at a density of 2×10$^5$ cells per dish in 35 mm dishes containing coverslips. The following day the cells were washed once with OptiMEM, then fed with 1 mL OptiMEM containing 1 μM PNA or PS-ODN, either alone, mixed with one of the 4 liposome reagents or incorporated in DOPE/DDAB liposomes, as described above. After an overnight incubation, the PNA-treated cells were fixed in 3% formaldehyde/0.2% glutaraldehyde on ice. The coverslips were then mounted on objective glasses and the cells observed by fluorescence microscopy on a Leits Diaplan microscope. Micrographs were taken with Kodak Ektacrome 1600 ASA film.

EXAMPLE 38

Cellular Uptake of Conjugated PNAs

Four conjugated PNAs (Example 30–32 and 36) having the title formula were prepared following the standard procedure illustrated in Example 28. Lysine residues were incorporated into PNA's by using a modified MBHA resin (Dueholm, *J. Org. Chem.,* 1994, 59, 5767) using a Boc-Lys-ClCbz (ClCbz=2-chlorobenzyloxycarbonyl). The PNA oligomer was then extended with a protected Lys group that was previously fluoresceinated at the ε-amino group. Deprotection of the amino group followed by conjugation with a lipophilic group afforded the support bound conjugated PNA. Cleavage from the solid support afforded the free PNA conjugate having a fluorescent label. The lipophilic groups (R) investigated include adamantoyl, decanoyl, heptyl-succinyl and palmityl-succinyl groups (as shown in FIG. 1).

Stock solutions of the four conjugated PNAs were prepared by dissolving the PNAs in DMSO. Dilutions of these stock solutions were made in either water or OptiMEM (Gibco BRL). The human cell line HeLa was grown in RPMI 1640 medium containing Glluamax™, penicillin, stepomycin and fetal calf serum (10% v/v). On the day preceding the experiment, the cells were plated at a density of 2×10$^5$ cells per dish in 35 mm dishes containing coverslips. The next day the cells were rinsed once with OptiMEM, then fed with 3 μM PNA in 1 mL of OptiMEM and further incubuated. In order to visualie PNA uptake, the coverslips were washed twice with PBS and the cells were fixed for 15 minutes in 3% formaldehyde/0.2% glutaraldehyde on ice. After washing twice with PBS, the coverslips were mounted on objective glasses using 90% glycerol in PBS, and the cells were observed by fluorescent microscopy on a Leitz Diaplan Microscope. Micrographs were taken with Kodak Ekachrome 1600 ASA film.

The four conjugated PNAs were Tested for uptake into human cells in culture. The PNAs were added directly to the cell culture medium. HeLa cells grown on coverslips were incubated with PNA (3 μm) in serum free medium overnight, then fixed and examined by fluorescence microscopy. Both The palmityl-succinyl and The heptyl-succinyl conjugated PNAs showed punctuate and spotted fluorescence in all cells. Generally, the spots were evenly distributed over the cell with a tendency of an enhanced staining at the edges of the cells, probably the cell membrane. The adamantoyl- and decanoyl-conjugated PNAs showed much less cell-associated fluorescence with large fluorescent aggregates seen outside the cells.

The palmityl-succinyl PNA conjugate was further studied by confocal microscopy to determine the exact location and distribution of the PNA conjugate inside the cell. A cell was selected from the above study and further scanned through 12 sections. The images confirm that the PNA conjugate was indeed taken up by the cells and distributed in spots throughout the cytoplasm. There was, apparently, no fluorescence in the nucleus. This pattern is indicative of the endocytotic pathway of uptake, implying that the PNA conjugates end up in endosomes The palmityl-succinyl PNA conjugate was also observed in a time course experiment Cells were incubated for different lengths of time in the presence of 3 $\mu$M of PNA. The uptake of the PNA conjugate by the cells increased with time up until 24 hours of incubation when the PNA-containing medium was replaced with fresh serum containing medium. After 48 hours intracellular PNA was concentrated in compartments of the cells, probably secondary lysosomes. After 72 hours there was virtually no PNA left inside the cells.

EXAMPLE 39

In Vitro Translation Assay Using Conjugated PNAs

PNA having the sequence R-Lys(Fluorescein)-TTT-AGC-TTC-CTT-AGC-Lys-NH$_2$ (SEQ ID NO:3) is complementary to the 15 nucleotides immediately 5' to the AUG start codon in CAT mRNA and the corresponding unconjugated PNA has previously been shown to be able to inhibit translation of CAT in vitro. The four conjugated PNAs of Example 38 (SEQ ID NO:2) were tested in this assay. All four conjugated PNAs specifically inhibited CAT translation at similar concentrations as the unconjugated PNA.

EXAMPLE 40

Preparation of Lysosome Constructs Using PNA Conjugates (SEQ ID NO:2)

Lysosome constructs were prepared using two of the conjugated PNAs having SEQ WD NO:2. The adamantoyl- and decanoyl-conjugated PNAs were combined with liposomes by a modification of the ethanol injection method described by Campbell in *Biotechniques,* 1995, 18, 1027. Following this method, 13.4 $\mu$mole of DOPE (dioleyl-L-$\alpha$-phosphatidylethanolamine) and 6.6 $\mu$mole of DDAB (dimethyldioctadecylammonium bromide) were dissolved in 1 mL of absolute ethanol. A solution of PNA (10 $\mu$L, 3 mM PNA/DMSO) was combined with 40 $\mu$L of the lipid mixture. The resulting 50 $\mu$L of reaction mixture was then rapidly added to 1 mL of sterile distilled H$_2$O while vortex mixing. The PNA concentration in the liposome mixture was thus 30 $\mu$M. For cell uptake experiments, 60 $\mu$L of the PNA-liposome mixture was added to 1 mL of OptiMEM and fed to the cells.

Incorporation of the conjugated PNAs into the liposome constructs was verified by fluorescent microscopy. The fluorescent micrographs showed spots of fluorescence associated with the cells as observed for the PNA conjugates. In addition, a more diffuse fluorescence was observed throughout the cells with fluorescence observed in the nuclei of some cells.

When other cell lines were used (COS-7, green monkey kidney derived cells; and NIH 3T3, mouse fibroblast cells) identical uptake patterns were observed.

EXAMPLE 41

Cellular Uptake of an Adamantyl-Conjugated PNA

The cellular uptake of an adamanyl-PNA (prepared according to Examples 35 or 36) was determined, and was also compared to the uptake of a phosphorolioate oligonucleotide. The adamantyl-conjugated PNA and oligonucleotide were added directly to subconfluent Hela cells at 1 $\mu$M concentrations and left over night. The cells were next fixed and uptake visualized by fluorescence microscopy. The oligonucleotide exhibited fine punctuate fluorescence, mainly confined to clusters in the cytoplasm of the cells and absent from the nuclei. With the PNA, punctuate fluorescence was similarly observed. However, the spots were somewhat larger and present both in the cytoplasm and on the cell membrane.

In an attempt to improve uptake of the adamantyl-PNA, the PNA was combined with various commercially available cationic liposomes normally used for transfection of DNA. In addition, PNA-containing liposomes composed of the lipids DOPE and DDAB were also prepared. In theory, the hydrophobic adamantyl-group of the PNA should insert into the lipid layer of the liposomes and thus entrap the PNA. The liposomes were prepared by a simple ethanol injection technique, which was reported to be efficient for the transport of plasmid DNA into cells. The different PNA-liposome mixtures were fed to cells with a final PNA concentration of 1 $\mu$M and incubated over night. The presence of either of the liposome reagents or the DOPE/DDAB liposomes resulted in a much more diffuse fluorescence inside the cells, compared to when the PNA was added alone. However, the fluorescence was still confined to the cytoplasm with no sign of nuclear upake. In contrast, when the oligonucleotide was mixed with Lipofectamine™ and fed to the cells at a concentration of 1 $\mu$M, the majority of the cells had fluorescently stained nuclei.

In conclusion, adding adamantyl-conjugated PNA to cells resulted in an uptake pattern reminiscent of an endocytotic pathway, where the PNA ends up in endosomal or lysosomal compartments of the cell. When PNA is pre-mixed with liposome transfection reagents or incorporated into DOPE/DDAB liposomes, it is distributed throughout the cell cytoplasm in a much more diffuse fashion.

Those skilled in the art will appreciate that numerous changes and modifications may be made to the preferred embodiments of the present invention and that such changes and modifications may be made without departing from the spirit of the invention. It is therefore intended that the appended claims cover all such equivalent variations as fall within the true spirit and scope of the invention.

What is claimed is:

1. A peptide nucleic acid having formula:

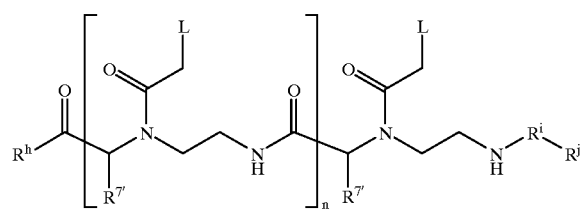

wherein:

each L is, independently, a naturally-occurring nucleobase or a non-naturally-occurring nucleobase;

each $R^{7'}$ is hydrogen or the side chain of a naturally-occurring or non-naturally-occurring amino acid, at least one $R^{7'}$ being the side chain of a naturally-occurring or non-naturally-occurring amino acid;

$R^h$ is OH, $NH_2$, or $NHLysNH_2$;

each of $R^i$ and $R^j$ is, independently, alkyl, lipid or steroid; or $R^i$ and $R^j$, together, are alkyl, lipid or steroid; and n is an integer from 1 to 30.

2. The peptide nucleic acid of claim 1 wherein at least one of said $R^{7'}$ is the side chain of a naturally-occurring amino acid.

3. The peptide nucleic acid of claim 2 wherein at least one $R^{7'}$ is the side chain of D-lysine.

4. The peptide nucleic acid of claim 1 wherein $R^{7'}$ is the side chain of an amino acid and the carbon atom to which the side chain is attached is stereochemically enriched.

5. A composition comprising a peptide nucleic acid incorporated into a liposonie, said peptide nucleic acid having formula:

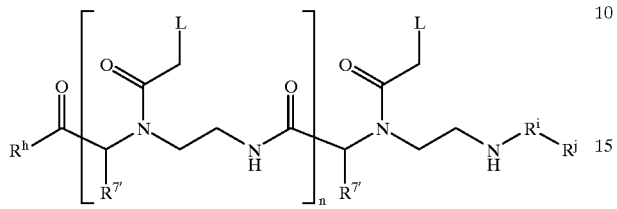

wherein:

each L is, independently, a naturally-occurring nucleobase or a non-naturally-occurring nucleobase;

each $R^{7'}$ is hydrogen or the side chain of a naturally-occurring or non-naturally-occurring amino acid;

$R^h$ is OH, $NH_2$, or $NHLysNH_2$;

each of $R^i$ and $R^j$ is, independently, alkyl, lipid or steroid; or $R^i$ and $R^j$, together, alkyl, lipid or steroid; and n is an integer from 1 to 30.

6. The composition of claim 5 wherein at least one of said $R^{7'}$ is the side chain of a naturally-occurring amino acid.

7. The composition of claim 6 wherein said amino acid is D-lysine.

8. The composition of claim 5 wherein $R^{7'}$ is the side chain of an amino acid and the carbon atom to which the side chain is attached is stereochemically enriched.

* * * * *